US011528911B2

(12) United States Patent
Grandlic et al.

(10) Patent No.: US 11,528,911 B2
(45) Date of Patent: Dec. 20, 2022

(54) COMPOSITIONS AND METHODS FOR CONTROLLING HEAD BLIGHT DISEASE

(71) Applicant: MONSANTO TECHNOLOGY LLC, St. Louis, MO (US)

(72) Inventors: Christopher J. Grandlic, San Diego, CA (US); Wayne A. Green, Encinitas, CA (US); Janne S. Kerovuo, San Diego, CA (US); Ryan T. McCann, San Diego, CA (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 16/514,800

(22) Filed: Jul. 17, 2019

(65) Prior Publication Data

US 2019/0364906 A1 Dec. 5, 2019

Related U.S. Application Data

(60) Division of application No. 15/384,127, filed on Dec. 19, 2016, now Pat. No. 10,412,971, which is a continuation of application No. 13/557,034, filed on Jul. 24, 2012, now Pat. No. 10,405,554.

(60) Provisional application No. 61/511,467, filed on Jul. 25, 2011.

(51) Int. Cl.

*A01N 63/20* (2020.01)
*C12N 1/20* (2006.01)
*C12R 1/07* (2006.01)

(52) U.S. Cl.

CPC ............... *A01N 63/20* (2020.01); *C12N 1/20* (2013.01); *C12N 1/205* (2021.05); *C12R 2001/07* (2021.05)

(58) Field of Classification Search

CPC ........ A01N 63/00; A01N 25/00; A01N 63/10; A01N 63/20; C12N 1/20; C12N 5/04; C12N 1/205; C12R 1/07; C12R 1/01; C12R 2001/07; C12R 2001/01; A01C 1/06; A01H 5/00; A01H 5/10; C05G 3/60

See application file for complete search history.

(56) References Cited

U.S. PATENT DOCUMENTS

| | | | | |
|---|---|---|---|---|
| 3,911,837 A * | 10/1975 | Quick | A01C 23/023 111/120 |
| 5,491,077 A | 2/1996 | Shafiee et al. | |
| 5,503,652 A | 4/1996 | Kloepper et al. | |
| 5,994,266 A * | 11/1999 | Hobbs | A01N 25/22 424/408 |
| 6,175,059 B1 * | 1/2001 | Rush | C12N 15/8283 800/278 |
| 6,312,940 B1 | 11/2001 | Schisler et al. | |
| 6,599,503 B2 | 7/2003 | da Luz | |
| 7,001,755 B2 | 2/2006 | Schisler et al. | |
| 7,037,879 B2 | 5/2006 | Imada et al. | |
| 7,601,346 B1 | 10/2009 | Schisler et al. | |
| 7,615,366 B2 | 11/2009 | Kim et al. | |
| 8,652,490 B2 | 2/2014 | Hewlett et al. | |
| 2009/0175837 A1 | 7/2009 | Yuki et al. | |
| 2015/0320033 A1 * | 11/2015 | Schultz | C05B 17/00 47/57.6 |

FOREIGN PATENT DOCUMENTS

| | | | |
|---|---|---|---|
| BR | 0009629 | | 8/2002 |
| CN | 1766091 | | 5/2006 |
| CN | 101857848 | | 10/2010 |
| CN | 101993836 | | 3/2011 |
| EP | 1397033 | | 10/2007 |
| ES | 2272734 | | 3/2004 |
| JP | A-2011-102278 | | 5/2011 |
| JP | 4768308 | | 9/2011 |
| KR | 1020020090253 | | 8/2009 |
| KZ | 24974 | | 12/2011 |
| RU | 2170511 | C2 | 7/2001 |
| RU | 2235771 | C2 | 9/2004 |
| RU | 2284353 | | 9/2006 |
| WO | WO 2009/037242 | | 3/2009 |

OTHER PUBLICATIONS

Simon, UK et al. Intragenomic variation of fungal ribosomal genes is higher than previously thought. 2008. 25(11): 2251-2254. (Year: 2008).*
GenBank. Sequence for EU 343182.1. Direct Submission submitted on Dec. 11, 2007. (Year: 2007).*

Verkley, GJM et al. Mycosphaerella punctiformis revisited: morphology, phylogeny, and epitypification of the type species of the genus *Mycosphaerella* (*Dothideales, Ascomycota*). 2004. 108(11): 1271-1282. (Year: 2004).*

Scotti-Saintagne, C et al. Genome scanning for interspecific differentiation between two closely related oak species [*Quercus robur* L. and *Q. petraea* (Matt.) Liebl.]. Genetics. 2004. 168: 1615-1626. (Year: 2004).*
Garry, G et al. Effects of Ascochyta blight (Mycosphaerella pinodes) on the photosynthesizing leaf area and the photosynthetic efficiency of the green leaf area of dried-pea (*Pisum sativum*). Plant Pathology. 1998. 47: 473-479. (Year: 1998).*

(Continued)

*Primary Examiner* — Renee Claytor
*Assistant Examiner* — Susan E. Fernandez
(74) *Attorney, Agent, or Firm* — Dentons US LLP; Michelle Samonek, Esq.

(57) ABSTRACT

Compositions comprising microbiological strains and cultures and methods of use thereof are provided herein. Certain strains, cultures, and compositions thereof are useful for the control of head blight disease, for example, of various crop plants. Biological control compositions, and methods of use thereof to prevent, inhibit or treat the development of plant pathogens or disease and for preserving plant yield, are also provided.

18 Claims, No Drawings

Specification includes a Sequence Listing.

(56) References Cited

OTHER PUBLICATIONS

Maude, RB. Pea seed infection by Mycosphaerella pinodes and Ascochyta pisi and its control by seed soaks in thiram and captan suspension. Ann. Appl. Biol. 1966. 57: 193-200. (Year: 1966).*
Bacon et al. "Biological control of Fusarium moniliforme in maize," *Environ. Health. Perspect.*;, 109 Suppl 2:325-32; 2001.
Blagoveshchenskaya, E. Yu, "Endophytic fungi of cereals", Extended abstract of Cand. Sci. Dissertation, Moscow, 2006, 26 p.
Cavaglieri et al., "In vitro influence of bacterial mixtures on *Fusarium verticillioides* growth and fumonisin $B_1$ production: effect of seeds treatment on maize root colonization," *Letters in Applied Microbiology* 41:390-396, 2005.
Chan et al., "Identification of lipopeptide antibiotics of a *Bacillus subtilis* isolate and their control of *Fusarium graminearum* diseases in maize and wheat," *BioControl* 54:567-574, 2009.
Crane et al., "Ecology of *Bacillus amyloliquefaciens* on wheat florets in relation to biological control of FHB/DON," *Proceedings of the 2010 National Fusarium Head Blight Forum* pp. 77-78, 2010.
Dayan et al., "Natural products in crop protection," *Bioorganic and Medicinal Chem.*;4022-4034;2009.
Fatina, "The Application of Microbiological Medications in Agriculture," *Vestnik ASTU* 4(39):133-136, 2007.
Fatina, "The Application of Microbiological Medications in Agriculture," *Vestnik ASTU* 4(39):133-136, 2007. (English translation).
GenBank Accession No. AB050667, 2009.
GenBank Accession No. AB199317, 2005.
GenBank Accession No. AB365061, 2008.
GenBank Accession No. EF471221, 2007.
GenBank Accession No. EU343177, 2008.
GenBank Accession No. GQ478273.1, Aug. 12, 2009.
Griebenow et al., "Lyophilization-induced reversible changes in the secondary structure of proteins," *PNAS*; 92:10969-10976; 1995.
International Search Report from PCT/US/2012/48012, 2012.
Mages et al., "Identities of *Arthrobacter* spp. and Arthobacter-like bacteria encountered in human clinical specimens," *J of Clinical Microbiol*; 46(9)2980-2986; 2008.
Mikhailovna, "Perspective bacterial strains, producers of microbiopreparations for decreasing harmfulness of fusariosis in sunflower," Thesis for degree of Candidate of Biological Sciences, Sankt-Petersburg, 2009.
Mikhailovna, "Perspective bacterial strains, producers of microbiopreparations for decreasing harmfulness of fusariosis in sunflower," Thesis for degree of Candidate of Biological Sciences, Sankt-Petersburg, 2009. (English translation).
Muthomi et al., "Occurrence of wheat head blight and *Fusarium* species infecting wheat," *African Crop Sci Conf Proceedings,*: 8:863-867; 2007.
Office Action regarding Australian Application No. 2016259414, dated Oct. 10, 2017.
Office Action regarding Australian Application No. 2016259414, dated Mar. 2, 2018.
Office Action regarding Australian Application No. 2017248427, dated Jul. 27, 2018.
Office Action regarding Brazilian Application No. BR112014001815, dated Sep. 20, 2018.
Office Action regarding Japanese Application No. 2014-522946, dated Apr. 19, 2016.
Office Action regarding Kazakhstan Application No. 2014/1520.1, dated Aug. 21, 2015 (English translation).
Office Action regarding Russian Application No. 2014106863, dated Jul. 29, 2016.
Office Action regarding Russian Application No. 2014106863, dated Nov. 24, 2016.
Office Action regarding Russian Application No. 2014106863, dated Jun. 6, 2017.
Palazzini et al., "Osmotic stress adaptation, compatible solutes accumulation and biocontrol efficacy of two potential biocontrol agents on *Fusarium* head blight in wheat," *Biological Control* 51:370-376, 2009.
Palumbo et al., "Isolation of maize Soil and Rhizosphere Bacteria with Antagonistic Activity against *Aspergillus flavus* and *Fusarium verticilloides*," *J of Food Protection*; 70(7); 1615-1621; 2007.
Pereira et al., "Efficacyof bacterial seed treatments for the control of Fusarium verticillioides in maize," *BioControl*; 54:103-111; 2009.
Response to Final Office Action regarding U.S. Appl. No. 13/557,034, dated May 8, 2017.
Response to Final Office Action regarding U.S. Appl. No. 13/557,034, dated May 22, 2018.
Response to Final Office Action regarding U.S. Appl. No. 13/557,034, dated Aug. 21, 2018.
Response to Non-final Office Action regarding U.S. Appl. No. 13/557,034, dated Jan. 25, 2019.
Sakr, Aggressiveness of four Fusarium head blight species on wheat cultivars, *Advances in Horticulture Sci*; 31(3); 199-203; 2017.
Sheng et al., "Characterization of heavy metal-resistance endophytic bacteria from rape (*Brassica napus*) roots and their potential in promoting the growth and lead accumulation of rape," *Environmental Pollution*; 156:1164-1170; 2008.
Tarantul, "Glossary of biotechnology terms," IPC of Rospatent, Moscow, 2005.
USPTO: Final Office Action regarding U.S. Appl. No. 13/557,034, dated Feb. 6, 2017.
USPTO: Final Office Action regarding U.S. Appl. No. 13/557,034, dated Feb. 27, 2018.
USPTO: Non-Final Office Action regarding U.S. Appl. No. 13/557,034, dated Aug. 3, 2017.
USPTO: Non-Final Office Action regarding U.S. Appl. No. 13/557,034, dated Oct. 9, 2018.
USPTO; Advisory Action regarding U.S. Appl. No. 13/557,034, dated Jun. 13, 2018.
Zhang et al., "Survival of the biocontrol agents *Brevibacillus brevis* ZJY-1 and *Bacillus subtilis* ZJY-116 on the spikes of barley in the field," *Journal of Zhejiang University Science* 6B(8):770-777, 2005.
Janda et al., "16S Gene Sequencing for Bacterial Identification in the Diagnostic Library: Plusses, Perils, and Pitfalls", Journal of Clinical Microbiology, 45(9):, 2761-2764, 2007.
Russian Office Action regarding Russian App. No. 2020136616, dated Dec. 1, 2021.

* cited by examiner

SEQUENCE LISTING

<160> NUMBER OF SEQ ID NOS: 18

<210> SEQ ID NO 1
<211> LENGTH: 1430
<212> TYPE: DNA
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: encodes a 16S ribosomal RNA

<400> SEQUENCE: 1

```
acgctggcgg cgtgcttaac acatgcaagt cgaacggtga acacggagct tgctctgtgg      60
gatcagtggc gaacgggtga gtaacacgtg agcaacctgc ccctgactct gggataagcg     120
ctggaaacgg cgtctaatac tggatatgtg acgtgaccgc atggtctgcg tctggaaaga     180
atttcggttg gggatgggct cgcggcctat cagcttgttg gtgaggtaat ggctcaccaa     240
ggcgtcgacg ggtagccggc ctgagagggt gaccggccac actgggactg agacacggcc     300
cagactccta cgggaggcag cagtggggaa tattgcacaa tgggcgcaag cctgatgcag     360
caacgccgcg tgagggacga cggccttcgg gttgtaaacc tcttttagca gggaagaagc     420
gaaagtgacg gtacctgcag aaaaagcgcc ggctaactac gtgccagcag ccgcggtaat     480
acgtagggcg caagcgttat ccggaattat tgggcgtaaa gagctcgtag gcggtttgtc     540
gcgtctgctg tgaaatccgg aggctcaacc tccggcctgc agtgggtacg ggcagactag     600
agtgcggtag gggagattgg aattcctggt gtagcggtgg aatgcgcaga tatcaggagg     660
aacaccgatg gcgaaggcag atctctgggc cgtaactgac gctgaggagc gaaagggtgg     720
ggagcaaaca ggcttagata ccctggtagt ccaccccgta aacgttggga actagttgtg     780
gggtccattc cacggattcc gtgacgcagc taacgcatta agttccccgc ctggggagta     840
cggccgcaag gctaaaactc aaaggaattg acggggaccc gcacaagcgg cggagcatgc     900
ggattaattc gatgcaacgc gaagaacctt accaaggctt gacatatacg agaacgggcc     960
agaaatggtc aactctttgg acactcgtaa acaggtggtg catggttgtc gtcagctcgt    1020
gtcgtgagat gttgggttaa gtcccgcaac gagcgcaacc ctcgttctat gttgccagca    1080
cgtaatggtg ggaactcatg ggatactgcc ggggtcaact cggaggaagg tggggatgac    1140
gtcaaatcat catgccccett atgtcttggg cttcacgcat gctacaatgg ccggtacaaa    1200
gggctgcaat accgcgaggt ggagcgaatc ccaaaaagcc ggtcccagtt cggattgagg    1260
tctgcaactc gacctcatga agtcggagtc gctagtaatc gcagatcagc aacgctgcgg    1320
tgaatacgtt cccgggtctt gtacacaccg cccgtcaagt catgaaagtc ggtaacacct    1380
gaagccggtg gcctaacctt tgtggaggga gccgtcgaag gtgggatcgg               1430
```

<210> SEQ ID NO 2
<211> LENGTH: 2172
<212> TYPE: DNA
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: SGI Gene ID SG1MICG850682
<220> FEATURE:
<221> NAME/KEY: misc_feature
<223> OTHER INFORMATION: encodes the peptide sequence at SED ID NO 3

<400> SEQUENCE: 2

```
gtgtctgcgg ccggagagcg gctgtcgaga atagactcgg agattgtgaa tgccgagtat      60
tccgcccatc atctccaggt gcttgagggg ctcgaagctg tccgcaagcg cccgggcatg     120
tacatcgggt cgaacggctc gccgggcctc atgcactgcc tttgggagat catcgacaac     180
tctgtcgacg aggcggtggc aggcaacggc acgaagatcg acatcatcct gcactccgac     240
ggcagcgtcg aggtgcacga ccgcggtcgc ggcatccctg tcgacgtcga gccgcgcacc     300
ggtctcaccg gtgtcgaggt cgtctacacc aagctgcacg ccggaggaaa gttcggcggc     360
ggctcgtacg cggcatccgg tggactgcac ggtgtcggcg cctccgtcgt gaacgcgctc     420
tccgagcgcc tcgacgtcga ggtcgaccgc ggggcaagaa cctacgcgat gtcgttccat     480
cgcggtgagc ccggcatctt cacggactcc ggcgagaagc ggccggacgc cccgttcacg     540
ccgttcgagg agaacagcga gctgcgcgtc atcggcaagg cgccgcgtgg cgtgaccggc     600
acccgggtgc gctactgggc cgaccggcag atcttcacca aggatgcggc gttccagctc     660
tcggagctcg agacccgcgc acgccagacg gcgttcctcg ttcccggtct cgagatcgtc     720
gtcaaggacg cacgggcggc cggtcaggtc atccccgtcc cggactccga cggcgagacg     780
accgtcgtcg ggaccgatga gacctcgtac ctctacgagg gcggcatctc cgagttcgtc     840
gagtacctcg ccatcgaccc tcccgtgacc gacacctggc gtatccaggg cgagggcatg     900
ttcaaggaga ccgtgcccgt cctgcaggca gacggccaca tggtcgccac cgaggtggag     960
cgtgtgtgcg ccgtcgacat cgcgctgcgc tggggaccg gctacgacac ccgtgtgcgc    1020
tccttcgtga acatcatcgc gacgcccaag ggcggaaccc accagcaggg cttcgagcag    1080
gagctcctga aggtgctgcg ctcccaggtc gagcagaacg cccgccgtct gaaggtcggc    1140
aacgacaagc tggagaagga cgacgtcctc gccggcctca ccgccgtgct cacggtcaac    1200
gtgccggagc cgcagttcga gggccagacc aaggaagtgc tcggcacccc cgcggtgcgg    1260
cagatcgtgg cgcaggtgat ccgtaaggat ctggcgcagc gcttcagctc gaccaagcgc    1320
gacgacaaga accaggccac acagctgctc gacaagatcg tctccgagat gaaggcccgt    1380
gtctcggcgc gcgcccacaa ggagacgcag cgccgcaaga cgcgctgga gtcgtcgacg    1440 ctgccgacca agctcgtcga ctgccgcacg aacgaggtcg agcgcagcga gctcttcatc    1500
gtggagggcg actcggctct cggcaccgcc aagaacgcgc gcaacagcga gttccaggcg    1560 ctgctccccga tccagggaa gatcctcaac gtgcagaagg cctctgtcgg cgacatgctg    1620
tcgaacaccg agtgcgcgtc gatcatccag gtgatcggcg ccggatccgg acgcaccttc    1680
gacatcgatg cggcgcgcta cggcaaggtg atcctgatga gcgacgccga tgtcgacggc    1740
gcgcacatcc gtaccctgct gctcacgctg ttcttccgct acatgcgacc gctgatcgag    1800
cacgggcgtg tgttcgccgc ggtgccgccg ttgcaccggg tgatcgtgat gaacccgggg    1860
```

```
tccaagccga acgagacgat ctacacctac agcgagcagg agatgcacgc gctgctggcg    1920
aagctccgca aggccggcaa gcgctggcac gagccgatcc agcgctacaa gggtctcggt    1980
gagatggacg cggaacagct cgcgaacacc accatggacc gctccggccg tctgctgcgc    2040
cgtgtgcgca tggaagacgc cgaggccgcc ggtcgcgtgt tcgagctgct gatgggcaac    2100
gaggtcgcgc cgcgccgcga gttcatcatc gactcctccg accggttgtc gcgcgagtcc    2160
atcgacgcct ga                                                        2172
```

<210> SEQ ID NO 3
<211> LENGTH: 723
<212> TYPE: PRT
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: SGI peptide ID SG1MICT850682
<220> FEATURE:
<221> NAME/KEY: misc_feature
<223> OTHER INFORMATION: gyrase subunit B

<400> SEQUENCE: 3

```
Met Ser Ala Ala Gly Glu Arg Leu Ser Arg Ile Asp Ser Glu Ile Val
1               5                   10                  15

Asn Ala Glu Tyr Ser Ala His His Leu Gln Val Leu Glu Gly Leu Glu
            20                  25                  30

Ala Val Arg Lys Arg Pro Gly Met Tyr Ile Gly Ser Asn Gly Ser Pro
        35                  40                  45

Gly Leu Met His Cys Leu Trp Glu Ile Ile Asp Asn Ser Val Asp Glu
    50                  55                  60

Ala Val Ala Gly Asn Gly Thr Lys Ile Asp Ile Ile Leu His Ser Asp
65                  70                  75                  80

Gly Ser Val Glu Val His Asp Arg Gly Arg Gly Ile Pro Val Asp Val
                85                  90                  95

Glu Pro Arg Thr Gly Leu Thr Gly Val Glu Val Val Tyr Thr Lys Leu
            100                 105                 110

His Ala Gly Gly Lys Phe Gly Gly Gly Ser Tyr Ala Ala Ser Gly Gly
        115                 120                 125

Leu His Gly Val Gly Ala Ser Val Val Asn Ala Leu Ser Glu Arg Leu
    130                 135                 140

Asp Val Glu Val Asp Arg Gly Gly Lys Thr Tyr Ala Met Ser Phe His
145                 150                 155                 160

Arg Gly Glu Pro Gly Ile Phe Thr Asp Ser Gly Glu Lys Arg Pro Asp
                165                 170                 175

Ala Pro Phe Thr Pro Phe Glu Glu Asn Ser Glu Leu Arg Val Ile Gly
            180                 185                 190

Lys Ala Pro Arg Gly Val Thr Gly Thr Arg Val Arg Tyr Trp Ala Asp
        195                 200                 205

Arg Gln Ile Phe Thr Lys Asp Ala Ala Phe Gln Leu Ser Glu Leu Glu
    210                 215                 220

Thr Arg Ala Arg Gln Thr Ala Phe Leu Val Pro Gly Leu Glu Ile Val
225                 230                 235                 240

Val Lys Asp Ala Arg Ala Ala Gly Gln Val Ile Pro Val Pro Asp Ser
                245                 250                 255

Asp Gly Glu Thr Thr Val Val Gly Thr Asp Glu Thr Ser Tyr Leu Tyr
```

```
                260                 265                 270
Glu Gly Gly Ile Ser Glu Phe Val Glu Tyr Leu Ala Ile Asp Pro Pro
            275                 280                 285

Val Thr Asp Thr Trp Arg Ile Gln Gly Glu Gly Met Phe Lys Glu Thr
        290                 295                 300

Val Pro Val Leu Gln Ala Asp Gly His Met Val Ala Thr Glu Val Glu
305                 310                 315                 320

Arg Val Cys Ala Val Asp Ile Ala Leu Arg Trp Gly Thr Gly Tyr Asp
                325                 330                 335

Thr Arg Val Arg Ser Phe Val Asn Ile Ile Ala Thr Pro Lys Gly Gly
            340                 345                 350

Thr His Gln Gln Gly Phe Glu Gln Glu Leu Leu Lys Val Leu Arg Ser
        355                 360                 365

Gln Val Glu Gln Asn Ala Arg Arg Leu Lys Val Gly Asn Asp Lys Leu
    370                 375                 380

Glu Lys Asp Asp Val Leu Ala Gly Leu Thr Ala Val Leu Thr Val Asn
385                 390                 395                 400

Val Pro Glu Pro Gln Phe Gly Gln Thr Lys Glu Val Leu Gly Thr
                405                 410                 415

Pro Ala Val Arg Gln Ile Val Ala Gln Val Ile Arg Lys Asp Leu Ala
            420                 425                 430

Gln Arg Phe Ser Ser Thr Lys Arg Asp Asp Lys Asn Gln Ala Thr Gln
        435                 440                 445

Leu Leu Asp Lys Ile Val Ser Glu Met Lys Ala Arg Val Ser Ala Arg
    450                 455                 460

Ala His Lys Glu Thr Gln Arg Arg Lys Asn Ala Leu Glu Ser Ser Thr
465                 470                 475                 480

Leu Pro Thr Lys Leu Val Asp Cys Arg Thr Asn Glu Val Glu Arg Ser
                485                 490                 495

Glu Leu Phe Ile Val Glu Gly Asp Ser Ala Leu Gly Thr Ala Lys Asn
            500                 505                 510

Ala Arg Asn Ser Glu Phe Gln Ala Leu Leu Pro Ile Arg Gly Lys Ile
        515                 520                 525

Leu Asn Val Gln Lys Ala Ser Val Gly Asp Met Leu Ser Asn Thr Glu
    530                 535                 540

Cys Ala Ser Ile Ile Gln Val Ile Gly Ala Gly Ser Gly Arg Thr Phe
545                 550                 555                 560

Asp Ile Asp Ala Ala Arg Tyr Gly Lys Val Ile Leu Met Ser Asp Ala
                565                 570                 575

Asp Val Asp Gly Ala His Ile Arg Thr Leu Leu Leu Thr Leu Phe Phe
            580                 585                 590

Arg Tyr Met Arg Pro Leu Ile Glu His Gly Arg Val Phe Ala Ala Val
        595                 600                 605

Pro Pro Leu His Arg Val Ile Val Met Asn Pro Gly Ser Lys Pro Asn
    610                 615                 620

Glu Thr Ile Tyr Thr Tyr Ser Glu Gln Glu Met His Ala Leu Leu Ala
625                 630                 635                 640

Lys Leu Arg Lys Ala Gly Lys Arg Trp His Glu Pro Ile Gln Arg Tyr
                645                 650                 655

Lys Gly Leu Gly Glu Met Asp Ala Glu Gln Leu Ala Asn Thr Thr Met
            660                 665                 670

Asp Arg Ser Gly Arg Leu Leu Arg Arg Val Arg Met Glu Asp Ala Glu
        675                 680                 685
```

-continued

```
Ala Ala Gly Arg Val Phe Glu Leu Leu Met Gly Asn Glu Val Ala Pro
        690                 695                 700

Arg Arg Glu Phe Ile Ile Asp Ser Ser Asp Arg Leu Ser Arg Glu Ser
705                 710                 715                 720

Ile Asp Ala

<210> SEQ ID NO 4
<211> LENGTH: 3504
<212> TYPE: DNA
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: SGI Gene ID SG1MICG850290
<220> FEATURE:
<221> NAME/KEY: misc_feature
<223> OTHER INFORMATION: encodes the peptide sequence at SEQ ID NO 5

<400> SEQUENCE: 4
ttggctgctg ctcgcaacgc atccacatcc accaccacca agaacggacg cggagcttcc     60
cgtctttcgt tcgccaagat ctccgacacg ctgacggtcc ctgaccttct cgccctgcag    120
accgaatcct tcggttggct ggtcggcaac gacgcctgga aggcgcgcgt ggccgaggcc    180
aagaagcagg ggcgcaccga cgtcaacgag aacagcggtc tgggcgagat cttcgaggag    240
atctctccga tcgaggacct cggcgagacg atgcagctgt cgttcacgaa ccctacctc    300 gagccggaga agtactccat cgaggagtgc aaggagcgtg gcaagaccta cgccgctccg    360
ctgtacgtcg aggccgagtt catgaaccac ctcacgggtg agatcaagac ccagacggtc    420
ttcatgggcg acttcccgct gcagaccgac aagggaacgt tcatcatcaa cggctccgag    480
cgcgtcgtcg tctcgcagct ggtgcgttcg cccggtgtct acttcgacaa gaccccccgac   540 aagacgtccg acaaggacat cgtctcggca cgcgtcatcc cgagccgtgg tgcctggctc   600
gagttcgaga tcgacaagcg cgaccaggtc ggcgtgcgcg tcgaccgcaa gcgcaagcag   660
tcggtcacgg tcttcctcaa ggcgctgggc atgaccagcg aggagatcct cgccgagttc   720
gccggctaca cctcgatcga ggagacgctc gcgaaggaca cgatcgtcac gaaggaagat   780
gcgctccgcg acatctaccg caagctccgt ccgggcgagc aggtcgccgc cgaggccgcc   840
cgcgcgctcc tggacaactt ctacttcaac ccgaagcgct acgacctggc caaggtcggt   900
cgctacaaga tcaaccacaa gctgggcctg accagccgc tgaactcgtc ggtcctgacc   960
gtcgaagaca tcgtggccac gatcaagtac ctggtgcgtc tgcacgccgg caccgaggag  1020
accttcacgg gcatccgcgg tggtaagaag gccgagatcc gtctcgcgac cgacgacatc  1080
gacaacttcg gcaaccgtcg catccgcgcg gtcggcgagc tgatccagaa ccaggtccgc  1140
accggtctct cccgcatgga gcgcgtcgtc cgcgagcgca tgaccacgca ggacatcgag  1200
gcgatcacgc cgcagaccct gatcaacgtg cgccccgtcg tcgccgcgat caaggagttc  1260
ttcggaacgt cgcagctgtc gcagttcatg gaccagaaca accgctcgc gggtctgacg  1320 aacaagcgtc gtctgtctgc gctcggcccc ggtggtctct cgcgagaccg cgccggcgtc  1380
gaggtccgtg acgtccaccc ctcgcactac ggccgcatgt gcccgatcga gactccggaa  1440
ggcccgaaca tcggtctgat cggtgctctc gcgaccttcg cgcgcatcaa ctcgttcgga  1500
ttcatcgaga cccgtaccg caaggtcgtc gacggtgtcg tgaccgacca gatcgactac  1560
ctgacggctt ccgaagaggt cgacttcaac atcgcgcagg ccaacgcccc gctcgatgcc  1620
```

```
aagggtcgct tccgcgagag ccacgtcctg gcccgcccca agggtggcag cggcgaggtc    1680
gacctgttcg tccccgagga gatcggctac atcgacgtct cccgcgcca gatggtgtcg    1740 gtcgcgacct cgctcgtgcc cttcctcgag cacgacgacg cacagcgcgc cctcatgggt    1800
gccaacatgc agcgtcaggc tgtgccgctg ctgcgcagcg actcgccgct cgtcggaacc    1860
ggtatggagg gctacacggc catcgacgcc ggtgacgtgc tcaccgccga aaggccggt    1920 gtcgtctccg aggtctccgc agaccgcgtc gtcgtcatgc tcgacgaggg cggaacgcag    1980
gagtaccacc tgcgcaagtt cgaccgctcc aaccagggca cgtcgtacaa ccagaaggtc    2040
gtcgtcaccg ccggtgagcg cgtcgaggtc ggagaggtca tcgccgatgg ccccgccacc    2100
gagaacggcg agctggccct cggaaagaac ctcctcgtcg cgttcatgac gtgggagggc    2160
tacaacttcg aggacgcgat catcctgagc caggacctgg tgaaggacga caccctctcc    2220
tcgatccaca tcgaggagta cgaggtcgat gctcgcgaca ccaagctcgg caaggaggag    2280
atcacgcgtg acctccccaa cgtcagcccg gagctgctga aggacctcga cgagcgcggc    2340
atcatccgca tcggtgccga ggtccgccct ggcgacatcc tcgtcggcaa ggtcacgccg    2400
aagggtgaga ccgagctgtc ggccgaggag cgcctgctcc gcgcgatctt caacgagaag    2460
agccgcgaag tccgtgacac ctcgctgaag gtgccccacg gtgagcaggg cacgatcatc    2520
gccgtcaagg agttcaacgc tgaggacggc gacgacgagc tcggctccgg cgtcaaccgc    2580
cgcgtcgtgg tctacatcgc ccagaagcgc aagatcaccg agggtgacaa gctcgccggc    2640
cgtcacggca acaagggtgt catcgcgaag atcctcccga tcgaggacat gccgttcctt    2700
tcggacggta ccccggtcga catcgtgctg aacccgctcg gtatccccgg tcgaatgaac    2760
ttcggtcagg tcctggagac ccacctcggg tggatcgcga agcagggctg gaaggtcgag    2820
ggcaacccgg agtgggctgt gaagctcccg aaggacgcat cgaggccgc ccccggcacg    2880 aaggtcgcca ccccggtgtt cgacggtgcg agcgaggagg agatcgctgg tctcctcgac    2940
gcgaccaccc cgacccgtga cggcgtccgc ctgatcgact cgagcggcaa gacgcagctg    3000
ttcgacggtc gttcgggtga gccgttcccg gcgccgatct ccgtgggcta catgtacatc    3060
ctgaagctgc accacctggt cgacgacaag atccacgcac gttccacggg tccgtactcg    3120
atgatcaccc agcagccgct cggtggtaag gcgcagttcg gtggacagcg cttcggtgag    3180
atggaggtgt gggccctcga ggcctacggc gccgcatacg cgctccagga gctcctcacg    3240
atcaagtccg acgacatcct cggccgcgtc aaggtgtacg aggcgatcgt caagggcgag    3300
aacatccagg agcccggcat ccccgagtcg ttcaaggtgc tcatgaagga gatgcagtcg    3360
ctctgcctga acgtcgaggt cctctcggcc gacggcacgc tggtcaacct ccgcgacacc    3420
gacgacgagg cgttccgcgc gcgggaagag ctcggtatca acatctccag ccgcttcgag    3480
gccgcctcga tcgacgagat ctaa                                           3504
```

<210> SEQ ID NO 5
<211> LENGTH: 1167
<212> TYPE: PRT
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: SGI peptide ID SG1MICT850290
<220> FEATURE:
<221> NAME/KEY: misc_feature
<223> OTHER INFORMATION: RNA-polymerase subunit B

<400> SEQUENCE: 5

```
Met Ala Ala Ala Arg Asn Ala Ser Thr Ser Thr Thr Thr Lys Asn Gly
1               5                   10                  15

Arg Gly Ala Ser Arg Leu Ser Phe Ala Lys Ile Ser Asp Thr Leu Thr
            20                  25                  30

Val Pro Asp Leu Leu Ala Leu Gln Thr Glu Ser Phe Gly Trp Leu Val
        35                  40                  45

Gly Asn Asp Ala Trp Lys Ala Arg Val Ala Glu Ala Lys Lys Gln Gly
    50                  55                  60

Arg Thr Asp Val Asn Glu Asn Ser Gly Leu Gly Glu Ile Phe Glu Glu
65                  70                  75                  80

Ile Ser Pro Ile Glu Asp Leu Gly Glu Thr Met Gln Leu Ser Phe Thr
                85                  90                  95

Asn Pro Tyr Leu Glu Pro Glu Lys Tyr Ser Ile Glu Glu Cys Lys Glu
            100                 105                 110

Arg Gly Lys Thr Tyr Ala Ala Pro Leu Tyr Val Glu Ala Glu Phe Met
        115                 120                 125

Asn His Leu Thr Gly Glu Ile Lys Thr Gln Thr Val Phe Met Gly Asp
    130                 135                 140

Phe Pro Leu Gln Thr Asp Lys Gly Thr Phe Ile Ile Asn Gly Ser Glu
145                 150                 155                 160

Arg Val Val Val Ser Gln Leu Val Arg Ser Pro Gly Val Tyr Phe Asp
                165                 170                 175

Lys Thr Pro Asp Lys Thr Ser Asp Lys Asp Ile Val Ser Ala Arg Val
            180                 185                 190

Ile Pro Ser Arg Gly Ala Trp Leu Glu Phe Glu Ile Asp Lys Arg Asp
        195                 200                 205

Gln Val Gly Val Arg Val Asp Arg Lys Arg Lys Gln Ser Val Thr Val
    210                 215                 220

Phe Leu Lys Ala Leu Gly Met Thr Ser Glu Glu Ile Leu Ala Glu Phe
225                 230                 235                 240

Ala Gly Tyr Thr Ser Ile Glu Glu Thr Leu Ala Lys Asp Thr Ile Val
                245                 250                 255

Thr Lys Glu Asp Ala Leu Arg Asp Ile Tyr Arg Lys Leu Arg Pro Gly
            260                 265                 270

Glu Gln Val Ala Ala Glu Ala Arg Ala Leu Leu Asp Asn Phe Tyr
        275                 280                 285

Phe Asn Pro Lys Arg Tyr Asp Leu Ala Lys Val Gly Arg Tyr Lys Ile
290                 295                 300

Asn His Lys Leu Gly Leu Asp Gln Pro Leu Asn Ser Ser Val Leu Thr
305                 310                 315                 320

Val Glu Asp Ile Val Ala Thr Ile Lys Tyr Leu Val Arg Leu His Ala
                325                 330                 335

Gly Thr Glu Glu Thr Phe Thr Gly Ile Arg Gly Gly Lys Lys Ala Glu
            340                 345                 350

Ile Arg Leu Ala Thr Asp Ile Asp Asn Phe Gly Asn Arg Arg Ile
        355                 360                 365

Arg Ala Val Gly Glu Leu Ile Gln Asn Gln Val Arg Thr Gly Leu Ser
    370                 375                 380

Arg Met Glu Arg Val Val Arg Glu Arg Met Thr Thr Gln Asp Ile Glu
385                 390                 395                 400

Ala Ile Thr Pro Gln Thr Leu Ile Asn Val Arg Pro Val Val Ala Ala
```

```
                    405                 410                 415
Ile Lys Glu Phe Phe Gly Thr Ser Gln Leu Ser Gln Phe Met Asp Gln
                420                 425                 430

Asn Asn Pro Leu Ala Gly Leu Thr Asn Lys Arg Arg Leu Ser Ala Leu
            435                 440                 445

Gly Pro Gly Gly Leu Ser Arg Asp Arg Ala Gly Val Glu Val Arg Asp
        450                 455                 460

Val His Pro Ser His Tyr Gly Arg Met Cys Pro Ile Glu Thr Pro Glu
465                 470                 475                 480

Gly Pro Asn Ile Gly Leu Ile Gly Ala Leu Ala Thr Phe Ala Arg Ile
                485                 490                 495

Asn Ser Phe Gly Phe Ile Glu Thr Pro Tyr Arg Lys Val Val Asp Gly
            500                 505                 510

Val Val Thr Asp Gln Ile Asp Tyr Leu Thr Ala Ser Glu Glu Val Asp
        515                 520                 525

Phe Asn Ile Ala Gln Ala Asn Ala Pro Leu Asp Ala Lys Gly Arg Phe
530                 535                 540

Arg Glu Ser His Val Leu Ala Arg Pro Lys Gly Gly Ser Gly Glu Val
545                 550                 555                 560

Asp Leu Phe Val Pro Glu Glu Ile Gly Tyr Ile Asp Val Ser Pro Arg
                565                 570                 575

Gln Met Val Ser Val Ala Thr Ser Leu Val Pro Phe Leu Glu His Asp
            580                 585                 590

Asp Ala Gln Arg Ala Leu Met Gly Ala Asn Met Gln Arg Gln Ala Val
        595                 600                 605

Pro Leu Leu Arg Ser Asp Ser Pro Leu Val Gly Thr Gly Met Glu Gly
610                 615                 620

Tyr Thr Ala Ile Asp Ala Gly Asp Val Leu Thr Ala Glu Lys Ala Gly
625                 630                 635                 640

Val Val Ser Glu Val Ser Ala Asp Arg Val Val Met Leu Asp Glu
                645                 650                 655

Gly Gly Thr Gln Glu Tyr His Leu Arg Lys Phe Asp Arg Ser Asn Gln
            660                 665                 670

Gly Thr Ser Tyr Asn Gln Lys Val Val Thr Ala Gly Glu Arg Val
        675                 680                 685

Glu Val Gly Glu Val Ile Ala Asp Gly Pro Ala Thr Glu Asn Gly Glu
        690                 695                 700

Leu Ala Leu Gly Lys Asn Leu Leu Val Ala Phe Met Thr Trp Glu Gly
705                 710                 715                 720

Tyr Asn Phe Glu Asp Ala Ile Ile Leu Ser Gln Asp Leu Val Lys Asp
                725                 730                 735

Asp Thr Leu Ser Ser Ile His Ile Glu Tyr Glu Val Asp Ala Arg
            740                 745                 750

Asp Thr Lys Leu Gly Lys Glu Ile Thr Arg Asp Leu Pro Asn Val
        755                 760                 765

Ser Pro Glu Leu Leu Lys Asp Leu Asp Glu Arg Gly Ile Ile Arg Ile
770                 775                 780

Gly Ala Glu Val Arg Pro Gly Asp Ile Leu Val Gly Lys Val Thr Pro
785                 790                 795                 800

Lys Gly Glu Thr Glu Leu Ser Ala Glu Glu Arg Leu Leu Arg Ala Ile
            805                 810                 815

Phe Asn Glu Lys Ser Arg Glu Val Arg Asp Thr Ser Leu Lys Val Pro
        820                 825                 830
```

His Gly Glu Gln Gly Thr Ile Ile Ala Val Lys Glu Phe Asn Ala Glu
         835                 840                 845

Asp Gly Asp Asp Glu Leu Gly Ser Gly Val Asn Arg Val Val Val
    850                 855                 860

Tyr Ile Ala Gln Lys Arg Lys Ile Thr Glu Gly Asp Lys Leu Ala Gly
865                 870                 875                 880

Arg His Gly Asn Lys Gly Val Ile Ala Lys Ile Leu Pro Ile Glu Asp
                885                 890                 895

Met Pro Phe Leu Ser Asp Gly Thr Pro Val Asp Ile Val Leu Asn Pro
        900                 905                 910

Leu Gly Ile Pro Gly Arg Met Asn Phe Gly Gln Val Leu Glu Thr His
        915                 920                 925

Leu Gly Trp Ile Ala Lys Gln Gly Trp Lys Val Glu Gly Asn Pro Glu
    930                 935                 940

Trp Ala Val Lys Leu Pro Lys Asp Ala Phe Glu Ala Ala Pro Gly Thr
945                 950                 955                 960

Lys Val Ala Thr Pro Val Phe Asp Gly Ala Ser Glu Glu Glu Ile Ala
                965                 970                 975

Gly Leu Leu Asp Ala Thr Thr Pro Thr Arg Asp Gly Val Arg Leu Ile
        980                 985                 990

Asp Ser Ser Gly Lys Thr Gln Leu Phe Asp Gly Arg Ser Gly Glu Pro
    995                 1000                1005

Phe Pro Ala Pro Ile Ser Val Gly Tyr Met Tyr Ile Leu Lys Leu
    1010                1015                1020

His His Leu Val Asp Asp Lys Ile His Ala Arg Ser Thr Gly Pro
    1025                1030                1035

Tyr Ser Met Ile Thr Gln Gln Pro Leu Gly Gly Lys Ala Gln Phe
    1040                1045                1050

Gly Gly Gln Arg Phe Gly Glu Met Glu Val Trp Ala Leu Glu Ala
    1055                1060                1065

Tyr Gly Ala Ala Tyr Ala Leu Gln Glu Leu Leu Thr Ile Lys Ser
    1070                1075                1080

Asp Asp Ile Leu Gly Arg Val Lys Val Tyr Glu Ala Ile Val Lys
    1085                1090                1095

Gly Glu Asn Ile Gln Glu Pro Gly Ile Pro Glu Ser Phe Lys Val
    1100                1105                1110

Leu Met Lys Glu Met Gln Ser Leu Cys Leu Asn Val Glu Val Leu
    1115                1120                1125

Ser Ala Asp Gly Thr Leu Val Asn Leu Arg Asp Thr Asp Asp Glu
    1130                1135                1140

Ala Phe Arg Ala Ala Glu Glu Leu Gly Ile Asn Ile Ser Ser Arg
    1145                1150                1155

Phe Glu Ala Ala Ser Ile Asp Glu Ile
    1160                1165

<210> SEQ ID NO 6
<211> LENGTH: 1188
<212> TYPE: DNA
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: SGI Gene ID SGI1MICG851004
<220> FEATURE:

-continued

<221> NAME/KEY: misc_feature
<223> OTHER INFORMATION: encodes the peptide sequence at SEQ ID NO 7

<400> SEQUENCE: 6

```
ttgccgactc gatgtcggtg gcctctccta cggtggaaaa caagccgaag agccattacg    60
ccttgtcgga gagttgctcc caaccgggag cgccgcgaca gcctacaggc ggcaccacgc   120
gcgcagaagg agcacatcat gccatcaccc gccgaccgcg agaagtccct cgagaccgcc   180
ctcgcccaga tcgaccgcca gttcggaaag ggctcggtca tgcggctggg cagcgatgag   240
cgcgcccccg tggccgtcat ccccaccggc tccatcgccc tcgacgtcgc cctcggcgtc   300
ggaggactcc cgcgtggtcg catcgtcgag atctacggac cggagtcctc cggtaagacg   360
acgctcaccc tgcacgcgat cgcgaacgca cagcgtgccg gtggcatcgc ggcgttcatc   420
gacgccgagc acgcgctcga ccccgactac gccgccaagc tcggcgtcga catcgatgcg   480
ctcctggtct cgcagcccga cacgggtgag caggcgctcg agatcgccga catgctcgtg   540
cgctccggtg cgatcgacct catcgtcatc gactccgtcg cggccctcgt gccgcgcgcc   600
gagatcgagg gcgagatggg tgactcgcac gtcggtctgc aggctcgcct catgtcgcag   660
gcgctgcgaa agctcaccgg tggtctgaac cagacgaaca ccacgatgat cttcatcaac   720
cagctccgcg agaagatcgg tgtcttcttc ggttcgccgg agaccactgc cggcggtaag   780
gcgctcaagt tctacgcctc ggtccgcatg gacatccgtc gtatcgagac gctcaaggac   840
ggtactgacg ctgtcggtaa ccgcaccagg gtcaaggtcg tcaagaacaa gatggctccg   900
cctttcaagc aggccgagtt cgacatcctc tacggcgtcg gcatctcgcg cgagggaagc   960
ctgatcgact cggtgtcga gcatgcgatc gtcaagaagt ccggttcctg gtatacgtac  1020
gacggtgacc agctgggtca gggcaaggag aacgcgcgga cgttcctgct caacaacccc  1080
gacatcgcgc tggcgatcga gacgcagatc aagcagaagc tcggcatcgg cggtcccgcc  1140
gcggcgcctg ctgcggcaga cgagctcgct gagcgtcgtc cggcctga             1188
```

<210> SEQ ID NO 7
<211> LENGTH: 395
<212> TYPE: PRT
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: SGI peptide ID SG1MICT851004
<220> FEATURE:
<221> NAME/KEY: misc_feature
<223> OTHER INFORMATION: recombinase A

<400> SEQUENCE: 7

```
Met Pro Thr Arg Cys Arg Trp Pro Leu Leu Arg Trp Lys Thr Ser Arg
1               5                   10                  15

Arg Ala Ile Thr Pro Cys Arg Arg Val Ala Pro Asn Arg Glu Arg Arg
            20                  25                  30

Asp Ser Leu Gln Ala Ala Pro Arg Ala Gln Lys Glu His Ile Met Pro
        35                  40                  45

Ser Pro Ala Asp Arg Glu Lys Ser Leu Glu Thr Ala Leu Ala Gln Ile
    50                  55                  60

Asp Arg Gln Phe Gly Lys Gly Ser Val Met Arg Leu Gly Ser Asp Glu
65                  70                  75                  80

Arg Ala Pro Val Ala Val Ile Pro Thr Gly Ser Ile Ala Leu Asp Val
                85                  90                  95
```

Ala Leu Gly Val Gly Gly Leu Pro Arg Gly Arg Ile Val Glu Ile Tyr
            100                 105                 110

Gly Pro Glu Ser Ser Gly Lys Thr Thr Leu Thr Leu His Ala Ile Ala
        115                 120                 125

Asn Ala Gln Arg Ala Gly Gly Ile Ala Ala Phe Ile Asp Ala Glu His
    130                 135                 140

Ala Leu Asp Pro Asp Tyr Ala Ala Lys Leu Gly Val Asp Ile Asp Ala
145                 150                 155                 160

Leu Leu Val Ser Gln Pro Asp Thr Gly Glu Gln Ala Leu Glu Ile Ala
                165                 170                 175

Asp Met Leu Val Arg Ser Gly Ala Ile Asp Leu Ile Val Ile Asp Ser
            180                 185                 190

Val Ala Ala Leu Val Pro Arg Ala Glu Ile Glu Gly Glu Met Gly Asp
        195                 200                 205

Ser His Val Gly Leu Gln Ala Arg Leu Met Ser Gln Ala Leu Arg Lys
    210                 215                 220

Leu Thr Gly Gly Leu Asn Gln Thr Asn Thr Thr Met Ile Phe Ile Asn
225                 230                 235                 240

Gln Leu Arg Glu Lys Ile Gly Val Phe Phe Gly Ser Pro Glu Thr Thr
                245                 250                 255

Ala Gly Gly Lys Ala Leu Lys Phe Tyr Ala Ser Val Arg Met Asp Ile
            260                 265                 270

Arg Arg Ile Glu Thr Leu Lys Asp Gly Thr Asp Ala Val Gly Asn Arg
        275                 280                 285

Thr Arg Val Lys Val Val Lys Asn Lys Met Ala Pro Pro Phe Lys Gln
    290                 295                 300

Ala Glu Phe Asp Ile Leu Tyr Gly Val Gly Ile Ser Arg Glu Gly Ser
305                 310                 315                 320

Leu Ile Asp Phe Gly Val Glu His Ala Ile Val Lys Lys Ser Gly Ser
                325                 330                 335

Trp Tyr Thr Tyr Asp Gly Asp Gln Leu Gly Gln Gly Lys Glu Asn Ala
            340                 345                 350

Arg Thr Phe Leu Leu Asn Asn Pro Asp Ile Ala Leu Ala Ile Glu Thr
        355                 360                 365

Gln Ile Lys Gln Lys Leu Gly Ile Gly Gly Pro Ala Ala Ala Pro Ala
    370                 375                 380

Ala Ala Asp Glu Leu Ala Glu Arg Arg Pro Ala
385                 390                 395

```
<210> SEQ ID NO 8
<211> LENGTH: 2175
<212> TYPE: DNA
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:
<221> NAME/KEY: misc_feature
<223> OTHER INFORMATION: SGI Gene ID SG1MICG849768
<220> FEATURE:
<221> NAME/KEY: misc_feature
<223> OTHER INFORMATION: encodes the peptide sequence at SEQ ID NO 9

<400> SEQUENCE: 8
atgtacccca tgatcgatcc cgcactcgcc gacgccggcc tcggtgacgc cgaagacgac      60
gacttcgacg ccatcgagtc tcccgactcc cagctcccgg accaccgcta cctggatcgc     120
```

```
gagctgagct ggctcgcctt caaccagcgc gtaatggagc tcgccgagga tccgtcactg        180
cccgaactcg agcgggcgaa cttcctggcg atcttcgcca gcaacctcga cgagttcttc        240
atggtgcgcg tcgccggcct caagcgccgc atcatgaccg gcctggccgt gccgacgaac        300
atcggccgct ccccgtcga cgcgctcgcc gacatctccc gcgaagcgca cgccctgcag         360
ctgcgtcacg ccgaggcctg gacctcgctc gtgcgccccg ccctggccga ctccggcatc        420
gagatcacgg actggtccga gctgaccgac gacgagcgct ccggattgtc cgagtacttc        480
cagctccagg tcttcccggt gctgatgccg ctcgcggtcg accggcgca tccgttcccc         540 tacatctccg gcctgtcgct gaacctcgcg atccgcatcc gcaatgcccg caccgggcgc        600
caggagttcg cgcgcctcaa ggtgccgccc atgctccccc gcttcgtgga ggtgccgggc        660
ggcggcgaga tcaagcgctt cctgcgcctg gaggaactga tcgcgaacca cctcggcgac        720
ctgttccccg gcatggaggt gctcgaccac cacgcgttcc gcctcacccg caacgaagac        780
gtggagatcg aggaagacga gagcgagaac ctcatccagg cgctcgaggc cgagctgctg        840
cgccgtcgat tcggcccgcc gatccgcctc gagatcacgg acgacatgga cgaggtcacg        900
atggacctgc tcgtccgcga gctcgacatc accgacctgg aggtctaccg cctccccggt        960
ccgctcgacc tgcgcggact gttcgatctg tcccgcatcg accgtcccga cctgcgctac       1020
ccgccgcacc tgcccaccac ggccgtggcc ttccagcccg caggatcgag caaccgcgcc       1080
gacatcttca agcgatccg caagtcggat gtgctcgtgc accacccgta cgagtcgttc         1140
acgaccagcg tgcaggcgtt cctcgaacag gccgcccgcg accgcacgt gctcgccatc         1200 aagcagaccc tgtaccgcac ctcgggcgac agcccggtcg tgcaggcgct gatcgacgcg       1260
gccgaagccg gcaagcaggt gctggccctc gtcgaggtga aggcccgttt cgacgaggcc       1320
aacaacatcg tctgggcacg caagctcgag aaggccggcg tgcacgtggt ctacggtctc       1380
gtcggactca agacccactg caagctcgcc ctcgtcatcc gcgaggaaga ggggatgctg       1440
cgccactact cgcacgtcgg caccggcaac tacaaccca agaccagccg catctacgag        1500
gacttcggtc tgttcaccgc agacgcgcag gtcggcaaag acctgacacg cctgttcaac       1560
gagctcagcg gctacgcgat cgagaagaag ttcaagcgcc tgctggtcgc cccgctgcac       1620
ctgcgcaagg gcctcatccg ccagatcgac gccgagcgca ggaacgccga ggcggggatc       1680
cccgcgcaca tccgcatcaa ggtgaactcg atggtcgatg aggagatcat cgacgcgctc       1740
taccgcgcga gcgcggccgg ggtgaaggtc gacgtgtggg tgcgcggcat ctgcagcctg       1800
cgcaccgacc tcgacggcat cagtgacaac atcacggtgc gcagcatcct cggccgctac       1860
ctcgagcact cccgcatctt cgcgttcgag aacgccggcg acccgcaggt gtacatcggc       1920
agcgccgaca tgatgcaccg caacctcgac cgtcgtgtgg aggcgctggt gcgcgtcacc       1980
gacgccgacc acctcaagga actgcaggcg ttcttcgacc tcgcgatgga cgacggaacc       2040
tcgtcgtggc atctcggcgc cggcggcgtc tgggagcgcc acgccgtgaa cgccgacggc       2100
aagccgctga tcgacctgca ggataagacc atggggttga tccagcggcg ccgccgcgcg       2160
cgggcggttc gatga                                                        2175
```

<210> SEQ ID NO 9
<211> LENGTH: 724
<212> TYPE: PRT
<213> ORGANISM: Microbacterium sp.
<220> FEATURE:
<221> NAME/KEY: misc_feature
<223> OTHER INFORMATION: SGI bacterial isolate SGI-014-C06
<220> FEATURE:

<221> NAME/KEY: misc_feature
<223> OTHER INFORMATION: SGI peptide ID SG1MICT849768
<220> FEATURE:
<221> NAME/KEY: misc_feature
<223> OTHER INFORMATION: polyphosphate kinase

<400> SEQUENCE: 9

```
Met Tyr Pro Met Ile Asp Pro Ala Leu Ala Asp Ala Gly Leu Gly Asp
1               5                   10                  15

Ala Glu Asp Asp Asp Phe Asp Ala Ile Glu Ser Pro Asp Ser Gln Leu
            20                  25                  30

Pro Asp His Arg Tyr Leu Asp Arg Glu Leu Ser Trp Leu Ala Phe Asn
        35                  40                  45

Gln Arg Val Met Glu Leu Ala Glu Asp Pro Ser Leu Pro Glu Leu Glu
    50                  55                  60

Arg Ala Asn Phe Leu Ala Ile Phe Ala Ser Asn Leu Asp Glu Phe Phe
65                  70                  75                  80

Met Val Arg Val Ala Gly Leu Lys Arg Arg Ile Met Thr Gly Leu Ala
                85                  90                  95

Val Pro Thr Asn Ile Gly Arg Ser Pro Val Asp Ala Leu Ala Asp Ile
            100                 105                 110

Ser Arg Glu Ala His Ala Leu Gln Leu Arg His Ala Glu Ala Trp Thr
        115                 120                 125

Ser Leu Val Arg Pro Ala Leu Ala Asp Ser Gly Ile Glu Ile Thr Asp
    130                 135                 140

Trp Ser Glu Leu Thr Asp Asp Glu Arg Ser Gly Leu Ser Glu Tyr Phe
145                 150                 155                 160

Gln Leu Gln Val Phe Pro Val Leu Met Pro Leu Ala Val Asp Pro Ala
                165                 170                 175

His Pro Phe Pro Tyr Ile Ser Gly Leu Ser Leu Asn Leu Ala Ile Arg
            180                 185                 190

Ile Arg Asn Ala Arg Thr Gly Arg Gln Glu Phe Ala Arg Leu Lys Val
        195                 200                 205

Pro Pro Met Leu Pro Arg Phe Val Glu Val Pro Gly Gly Gly Glu Ile
    210                 215                 220

Lys Arg Phe Leu Arg Leu Glu Glu Leu Ile Ala Asn His Leu Gly Asp
225                 230                 235                 240

Leu Phe Pro Gly Met Glu Val Leu Asp His His Ala Phe Arg Leu Thr
                245                 250                 255

Arg Asn Glu Asp Val Glu Ile Glu Glu Asp Glu Ser Glu Asn Leu Ile
            260                 265                 270

Gln Ala Leu Glu Ala Glu Leu Leu Arg Arg Phe Gly Pro Pro Ile
        275                 280                 285

Arg Leu Glu Ile Thr Asp Asp Met Asp Glu Val Thr Met Asp Leu Leu
    290                 295                 300

Val Arg Glu Leu Asp Ile Thr Asp Leu Glu Val Tyr Arg Leu Pro Gly
305                 310                 315                 320

Pro Leu Asp Leu Arg Gly Leu Phe Asp Leu Ser Arg Ile Asp Arg Pro
                325                 330                 335

Asp Leu Arg Tyr Pro Pro His Leu Pro Thr Thr Ala Val Ala Phe Gln
            340                 345                 350

Pro Ala Gly Ser Ser Asn Arg Ala Asp Ile Phe Lys Ala Ile Arg Lys
        355                 360                 365

Ser Asp Val Leu Val His His Pro Tyr Glu Ser Phe Thr Thr Ser Val
    370                 375                 380
```

-continued

```
Gln Ala Phe Leu Glu Gln Ala Arg Asp Pro His Val Leu Ala Ile
385                 390                 395                 400

Lys Gln Thr Leu Tyr Arg Thr Ser Gly Asp Ser Pro Val Val Gln Ala
            405                 410                 415

Leu Ile Asp Ala Ala Glu Ala Gly Lys Gln Val Leu Ala Leu Val Glu
        420                 425                 430

Val Lys Ala Arg Phe Asp Glu Ala Asn Asn Ile Val Trp Ala Arg Lys
    435                 440                 445

Leu Glu Lys Ala Gly Val His Val Val Tyr Gly Leu Val Gly Leu Lys
450                 455                 460

Thr His Cys Lys Leu Ala Leu Val Ile Arg Glu Glu Glu Gly Met Leu
465                 470                 475                 480

Arg His Tyr Ser His Val Gly Thr Gly Asn Tyr Asn Pro Lys Thr Ser
                485                 490                 495

Arg Ile Tyr Glu Asp Phe Gly Leu Phe Thr Ala Asp Ala Gln Val Gly
            500                 505                 510

Lys Asp Leu Thr Arg Leu Phe Asn Glu Leu Ser Gly Tyr Ala Ile Glu
        515                 520                 525

Lys Lys Phe Lys Arg Leu Leu Val Ala Pro Leu His Leu Arg Lys Gly
    530                 535                 540

Leu Ile Arg Gln Ile Asp Ala Glu Arg Arg Asn Ala Glu Ala Gly Ile
545                 550                 555                 560

Pro Ala His Ile Arg Ile Lys Val Asn Ser Met Val Asp Glu Glu Ile
                565                 570                 575

Ile Asp Ala Leu Tyr Arg Ala Ser Ala Ala Gly Val Lys Val Asp Val
            580                 585                 590

Trp Val Arg Gly Ile Cys Ser Leu Arg Thr Asp Leu Asp Gly Ile Ser
        595                 600                 605

Asp Asn Ile Thr Val Arg Ser Ile Leu Gly Arg Tyr Leu Glu His Ser
610                 615                 620

Arg Ile Phe Ala Phe Glu Asn Ala Gly Asp Pro Gln Val Tyr Ile Gly
625                 630                 635                 640

Ser Ala Asp Met Met His Arg Asn Leu Asp Arg Arg Val Glu Ala Leu
                645                 650                 655

Val Arg Val Thr Asp Ala Asp His Leu Lys Glu Leu Gln Ala Phe Phe
            660                 665                 670

Asp Leu Ala Met Asp Asp Gly Thr Ser Ser Trp His Leu Gly Ala Gly
        675                 680                 685

Gly Val Trp Glu Arg His Ala Val Asn Ala Asp Gly Lys Pro Leu Ile
    690                 695                 700

Asp Leu Gln Asp Lys Thr Met Gly Leu Ile Gln Arg Arg Arg Ala
705                 710                 715                 720

Arg Ala Val Arg
```

<210> SEQ ID NO 10
<211> LENGTH: 1390
<212> TYPE: DNA
<213> ORGANISM: Microbacterium sp.
<220> FEATURE:
<221> NAME/KEY: misc_feature
<223> OTHER INFORMATION: SGI bacterial isolate SGI-005-G08
<220> FEATURE:
<221> NAME/KEY: misc_feature
<223> OTHER INFORMATION: encodes a 16S ribosomal RNA
<220> FEATURE:
<221> NAME/KEY: misc_feature

```
<222> LOCATION: (29)..(36)
<223> OTHER INFORMATION: n is a, c, g, t, or other
<220> FEATURE:
<221> NAME/KEY: misc_feature
<222> LOCATION: (38)..(41)
<223> OTHER INFORMATION: n is a, c, g, t, or other

<400> SEQUENCE: 10
aacggtgaac acggagcttg ctctgtggnn nnnnnngnnn ncgggtgagt aacacgtgag      60
caacctgccc ctgactctgg gataagcgct ggaaacggcg tctaatactg gatacgagta     120
gcgatcgcat ggtcagctac tggaaagatt ttttggttgg ggatgggctc gcggcctatc    180
agcttgttgg tgaggtaatg gctcaccaag gcgtcgacgg gtagccggcc tgagagggtg    240
accggccaca ctgggactga gacacggccc agactcctac gggaggcagc agtggggaat    300
attgcacaat gggcggaagc ctgatgcagc aacgccgcgt gagggatgac ggccttcggg    360
ttgtaaacct cttttagcag ggaagaagcg aaagtgacgg tacctgcaga aaaagcgccg    420
gctaactacg tgccagcagc cgcggtaata cgtagggcgc aagcgttatc cggaattatt    480
gggcgtaaag agctcgtagg cggtttgtcg cgtctgctgt gaaatcccga ggctcaacct    540
cgggcctgca gtgggtacgg gcagactaga gtgcggtagg ggagattgga attcctggtg    600
tagcggtgga atgcgcagat atcaggagga acaccgatgg cgaaggcaga tctctgggcc    660
gtaactgacg ctgaggagcg aaagggtggg gagcaaacag gcttagatac cctggtagtc    720
caccccgtaa acgttgggaa ctagttgtgg ggtccattcc acggattccg tgacgcagct    780
aacgcattaa gttccccgcc tggggagtac ggccgcaagg ctaaaactca aaggaattga    840
cggggacccg cacaagcggc ggagcatgcg gattaattcg atgcaacgcg aagaaccttta   900
ccaaggcttg acatatacga gaacgggcca gaaatggtca actctttgga cactcgtaaa    960
caggtggtgc atggttgtcg tcagctcgtg tcgtgagatg ttgggttaag tcccgcaacg   1020
agcgcaaccc tcgttctatg ttgccagcac gtaatggtgg gaactcatgg gatactgccg   1080
gggtcaactc ggaggaaggt ggggatgacg tcaaatcatc atgccccctta tgtcttgggc  1140
ttcacgcatg ctacaatggc cggtacaaag ggctgcaata ccgtgaggtg gagcgaatcc   1200
caaaaagccg gtcccagttc ggattgaggt ctgcaactcg acctcatgaa gtcggagtcg   1260
ctagtaatcg cagatcagca acgctgcggt gaatacgttc ccgggtcttg tacacaccgc   1320
ccgtcaagtc atgaaagtcg gtaacacctg aagccggtgg cctaaccctt gtggagggag   1380
ccgtcgaagg                                                           1390

<210> SEQ ID NO 11
<211> LENGTH: 532
<212> TYPE: DNA
<213> ORGANISM: Mycosphaerella sp.
<220> FEATURE:
<221> NAME/KEY: misc_feature
<223> OTHER INFORMATION: SGI bacterial isolate SGI-010-H11
<220> FEATURE:
<221> NAME/KEY: misc_feature
<223> OTHER INFORMATION: Internal transcribed spacer 1_5.8S ribosomal
      DNA
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t

<400> SEQUENCE: 11
```

```
cggagggatc attaatgagt gagggggcca cccccaacct ccnacccttt gtgaacgcat      60
catgttgctt cggggggcgac cctgccgttc gcggcattcc ccccggaggt catcaaaaca   120
ctgcattctt acgtcggagt aaaaagttaa tttaataaaa ctttcaacaa cggatctctt   180
ggttctggca tcgatgaaga acgcagcgaa atgcgataag taatgtgaat tgcagaattc   240
agtgaatcat cgaatctttg aacgcacatt gcgccccctg gtattccggg gggcatgcct   300
gttcgagcgt catttcacca ctcaagcctc gcttggtatt gggcgtcgcg agtctctcgc   360
gcgcctcaaa gtctccggct gttcggttcg tctcccagcg ttgtggcaac tatttcgcag   420
tggagtacga gtcgtggcgg ccgttaaatc tttcaaaggt tgacctcgga tcaggtaggg   480
atacccgctg aacttaagca tatcaataag cggaggaggt catagntgtt tc           532
```

<210> SEQ ID NO 12
<211> LENGTH: 1431
<212> TYPE: DNA
<213> ORGANISM: Variovorax sp.
<220> FEATURE:
<221> NAME/KEY: misc_feature
<223> OTHER INFORMATION: SGI bacterial isolate SGI-014-G01
<220> FEATURE:
<221> NAME/KEY: misc_feature
<223> OTHER INFORMATION: encodes a 16S ribosomal RNA

<400> SEQUENCE: 12

```
tgccttacac atgcaagtcg aacggcagcg cgggagcaat cctggcggcg agtggcgaac     60
gggtgagtaa tacatcggaa cgtgcccaat cgtgggggat aacgcagcga agctgtgct   120 aataccgcat acgatctacg gatgaaagca ggggatcgca agaccttgcg cgaatggagc   180
ggccgatggc agattaggta gttggtgagg taaaggctca ccaagccttc gatctgtagc   240
tggtctgaga ggacgaccag ccacactggg actgagacac ggcccagact cctacgggag   300
gcagcagtgg ggaattttgg acaatgggcg aaagcctgat ccagccatgc cgcgtgcagg   360
atgaaggcct tcgggttgta aactgctttt gtacggaacg aaacggcctt ttctaataaa   420
gagggctaat gacggtaccg taagaataag caccggctaa ctacgtgcca gcagccgcgg   480
taatacgtag ggtgcaagcg ttaatcggaa ttactgggcg taaagcgtgc gcaggcggtt   540
atgtaagaca gttgtgaaat cccccgggctc aacctgggaa ctgcatctgt gactgcatag   600
ctagagtacg gtagagggg atggaattcc gcgtgtagca gtgaaatgcg tagatatgcg   660
gaggaacacc gatggcgaag gcaatccccct ggacctgtac tgacgctcat gcacgaaagc   720
gtggggagca aacaggatta gataccctgg tagtccacgc cctaaacgat gtcaactggt   780
tgttgggtct tcactgactc agtaacgaag ctaacgcgtg aagttgaccg cctggggagt   840
acggccgcaa ggttgaaact caaaggaatt gacgggaccc cgcacaagcg gtggatgatg   900
tggtttaatt cgatgcaacg cgaaaaacct tacccacctt tgacatgtac ggaattcgcc   960
agagatggct tagtgctcga aagagaaccg taacacaggt gctgcatggc tgtcgtcagc  1020
tcgtgtcgtg agatgttggg ttaagtcccg caacgagcgc aacccttgtc attagttgct  1080
acattcagtt gggcactcta atgagactgc cggtgacaaa ccggaggaag gtggggatga  1140
cgtcaagtcc tcatggccct tataggtggg gctacacacg tcatacaatg gctggtacaa  1200
agggttgcca acccgcgagg gggagctaat cccataaaac cagtcgtagt ccggatcgca  1260
gtctgcaact cgactgcgtg aagtcggaat cgctagtaat cgtggatcag aatgtcacgg  1320
tgaatacgtt cccgggtctt gtacacaccg cccgtcacac catgggagcg ggttctgcca  1380
```

```
gaagtagtta gcttaaccgc aaggagggcg attaccacgg cagggttcgt g        1431
```

```
<210> SEQ ID NO 13
<211> LENGTH: 1424
<212> TYPE: DNA
<213> ORGANISM: Bacillus amyloliquefaciens
<220> FEATURE:
<221> NAME/KEY: misc_feature
<223> OTHER INFORMATION: SGI bacterial isolate SGI-015-F03
<220> FEATURE:
<221> NAME/KEY: misc_feature
<223> OTHER INFORMATION: encodes a 16S ribosomal RNA

<400> SEQUENCE: 13
ctggcggcgt gcctaataca tgcaagtcga gcggacagat gggagcttgc tccctgatgt    60
tagcggcgga cgggtgagta acacgtgggt aacctgcctg taagactggg ataactccgg   120
gaaaccgggg ctaataccgg atggttgtct gaaccgcatg gttcagacat aaaaggtggc   180
ttcggctacc acttacagat ggacccgcgg cgcattagct agttggtgag gtaacggctc   240
accaaggcga cgatgcgtag ccgacctgag agggtgatcg ccacactgg gactgagaca    300
cggcccagac tcctacggga ggcagcagta gggaatcttc cgcaatggac gaaagtctga   360
cggagcaacg ccgcgtgagt gatgaaggtt ttcggatcgt aaagctctgt tgttagggaa   420
gaacaagtgc cgttcaaata gggcggcacc ttgacggtac ctaaccagaa agccacggct   480
aactacgtgc cagcagccgc ggtaatacgt aggtggcaag cgttgtccgg aattattggg   540
cgtaaagggc tcgcaggcgg tttcttaagt ctgatgtgaa agcccccggc tcaaccgggg   600
agggtcattg gaaactgggg aacttgagtg cagaagagga gagtggaatt ccacgtgtag   660
cggtgaaatg cgtagagatg tggaggaaca ccagtggcga aggcgactct ctggtctgta   720
actgacgctg aggagcgaaa gcgtggggag cgaacaggat tagataccct ggtagtccac   780
gccgtaaacg atgagtgcta agtgttaggg ggtttccgcc cttagtgct gcagctaacg    840
cattaagcac tccgcctggg gagtacggtc gcaagactga aactcaaagg aattgacggg   900
ggcccgcaca agcggtggag catgtggttt aattcgaagc aacgcgaaga accttaccag   960
gtcttgacat cctctgacaa tcctagagat aggacgtccc cttcggggc agagtgacag  1020
gtggtgcatg gttgtcgtca gctcgtgtcg tgagatgttg ggttaagtcc cgcaacgagc  1080
gcaacccttg atcttagttg ccagcattca gttgggcact ctaaggtgac tgccggtgac  1140
aaaccggagg aaggtgggga tgacgtcaaa tcatcatgcc ccttatgacc tgggctacac  1200
acgtgctaca atggacagaa caaagggcag cgaaaccgcg aggttaagcc aatcccacaa  1260
atctgttctc agttcggatc gcagtctgca actcgactgc gtgaagctgg aatcgctagt  1320
aatcgcggat cagcatgccg cggtgaatac gttcccgggc cttgtacaca ccgcccgtca  1380
caccacgaga gtttgtaaca cccgaagtcg gtgaggtaac cttt                   1424
```

```
<210> SEQ ID NO 14
<211> LENGTH: 1425
<212> TYPE: DNA
<213> ORGANISM: Bacillus subtilis
<220> FEATURE:
<221> NAME/KEY: misc_feature
<223> OTHER INFORMATION: SGI bacterial isolate SGI-015-H06
<220> FEATURE:
<221> NAME/KEY: misc_feature
<223> OTHER INFORMATION: encodes a 16S ribosomal RNA

<400> SEQUENCE: 14
gctggcggcg tgcctaatac atgcaagtcg agcggacaga tgggagcttg ctccctgatg    60
```

```
ttagcggcgg acgggtgagt aacacgtggg taacctgcct gtaagactgg gataactccg    120
ggaaaccggg gctaataccg gatggttgtt tgaaccgcat ggttcagaca taaaaggtgg    180
cttcggctac cacttacaga tggacccgcg gcgcattagc tagttggtga ggtaacggct    240
caccaaggca acgatgcgta gccgacctga gagggtgatc ggccacactg ggactgagac    300
acggcccaga ctcctacggg aggcagcagt agggaatctt ccgcaatgga cgaaagtctg    360
acggagcaac gccgcgtgag tgatgaaggt tttcggatcg taaagctctg ttgttaggga    420
agaacaagtg ccgttcaaat agggcggcac cttgacggta cctaaccaga aagccacggc    480
taactacgtg ccagcagccg cggtaatacg taggtggcaa gcgttgtccg gaattattgg    540
gcgtaaaggg ctcgcaggcg gtttcttaag tctgatgtga aagcccccgg ctcaaccggg    600
gagggtcatt ggaaactggg gaacttgagt gcagaagagg agagtggaat tccacgtgta    660
gcggtgaaat gcgtagagat gtggaggaac accagtggcg aaggcgactc tctggtctgt    720
aactgacgct gaggagcgaa agcgtgggga gcgaacagga ttagataccc tggtagtcca    780
cgccgtaaac gatgagtgct aagtgttagg gggtttccgc cccttagtgc tgcagctaac    840
gcattaagca ctccgcctgg ggagtacggt cgcaagactg aaactcaaag gaattgacgg    900
gggcccgcac aagcggtgga gcatgtggtt taattcgaag caacgcgaag aaccttacca    960
ggtcttgaca tcctctgaca atcctagaga taggacgtcc ccttcggggg cagagtgaca    1020
ggtggtgcat ggttgtcgtc agctcgtgtc gtgagatgtt gggttaagtc cgcaacgag    1080 cgcaacccct tgatcttagtt gccagcattc agttgggcac tctaaggtga ctgccggtga    1140
caaaccggag gaaggtgggg atgacgtcaa atcatcatgc cccttatgac ctgggctaca    1200
cacgtgctac aatggacaga acaaagggca gcgaaaccgc gaggttaagc caatcccaca    1260
aatctgttct cagttcggat cgcagtctgc aactcgactg cgtgaagctg gaatcgctag    1320
taatcgcgga tcagcatgcc gcggtgaata cgttcccggg ccttgtacac accgcccgtc    1380
acaccacgag agtttgtaac acccgaagtc ggtgaggtaa ccttt    1425
```

<210> SEQ ID NO 15
<211> LENGTH: 37
<212> TYPE: DNA
<213> ORGANISM: Artificial sequence
<220> FEATURE:
<223> OTHER INFORMATION: PCR primer M13-ITS1

<400> SEQUENCE: 15

```
tgtaaaacga cggccagttt cgtaggtgaa cctgcgg    37
```

<210> SEQ ID NO 16
<211> LENGTH: 38
<212> TYPE: DNA
<213> ORGANISM: Artificial sequence
<220> FEATURE:
<223> OTHER INFORMATION: PCR primer ITS4-M13

<400> SEQUENCE: 16

```
caggaaacag ctatgacctc ctccgcttat tgatatgc    38
```

<210> SEQ ID NO 17
<211> LENGTH: 39
<212> TYPE: DNA
<213> ORGANISM: Artificial sequence
<220> FEATURE:
<223> OTHER INFORMATION: PCR primer M13-27F Bac

```
<400> SEQUENCE: 17
tgtaaaacga cggccagtta gagtttgatc ctggctcag                    39

<210> SEQ ID NO 18
<211> LENGTH: 37
<212> TYPE: DNA
<213> ORGANISM: Artificial sequence
<220> FEATURE:
<223> OTHER INFORMATION: PCR primer 1492R-M13 Bac

<400> SEQUENCE: 18
caggaaacag ctatgaccgg ttaccttgtt acgactt                      37
```

COMPOSITIONS AND METHODS FOR CONTROLLING HEAD BLIGHT DISEASE

CROSS-REFERENCES TO RELATED APPLICATIONS

This application is a divisional of U.S. patent application Ser. No. 15/384,127, filed Dec. 19, 2016, which is a continuation of U.S. patent application Ser. No. 13/557,034, filed Jul. 24, 2012, which claims priority under 35 U.S.C. § 119(e) to U.S. Provisional Patent Application Ser. No. 61/511,467, filed on Jul. 25, 2011, the entire contents of which are herein incorporated by reference.

INCORPORATION OF SEQUENCE LISTING

The material in the accompanying Sequence Listing is hereby incorporated by reference in its entirety. The accompanying file, named "SGI1520-1_ST25.txt", was created on Jul. 24, 2012 and is 52 Kb. The file can be accessed using Microsoft Word on a computer that uses Window OS.

FIELD OF THE INVENTION

The present invention relates to the biological control of phytopathogenic diseases. Specifically, it relates to compositions and methods useful for controlling head blight disease in cereal plants, such as wheat and barley.

BACKGROUND OF THE INVENTION

Head blight, also known as head scab, pink mold, whiteheads and tombstone scab, is a devastating disease afflicting wheat, barley, and several other cereal crops worldwide, particularly in USA, Europe and China. This disease can reach epidemic levels and cause extensive damage to grains, especially wheat and barley in humid and semi-humid cereal growing areas of the world, including India, Russia, France, Germany, and the United Kingdom. Particularly, wheat scab or head blight is one of the more damaging diseases of wheat in the United States. Nationwide, this disease has caused the wheat industry millions of dollars in yield losses. In the Midwest and High Plains, wheat scab is the major obstacle to wheat production in recent years. Head blight in addition to attacking wheat also attacks and reproduces on barley, oats, corn, and many other cereals.

This serious plant disease can be caused by several phytopathogens, but primarily by several species in the fungal genus *Fusarium*. For example, causal agents of the head blight disease in wheat include a number of different *Fusarium* species, e.g. *F. culmorum, F. graminearum* (teleomorph, *Gibberella zeae*), *F. avenaceum* (teleomorph, G. *avenacea*), *F. poae*, as well as by non-*Fusarium* pathogens such as *Microdochium nivale* (teleomorph, *Monographella nivalis*), and *Microdochium majus*. In the United States, Europe and most agronomically important areas of the world, the predominant causative agent of head blight is *Fusarium graminearum* (teleomorph, *Gibberella zeae* sensu strict).

These pathogens typically survive on plant debris. They invade and damage the spikelets of the grain head during flowering, thus preventing or partially impeding the development of grain in the grain head. As a result, the invading scab pathogen can either kill part of the grain head or the entire grain head. Some infected seeds are low in vigor and often fail to germinate. Infected seeds that germinate often die early in the seedling stage due to crown rot or root rot, causing poor stands in the following crop plant. Healthy seedlings can also become infected at emergence. In addition to poor, unthrifty stand, yield losses due to pathogen infestation can be quite high if conditions are favorable for development of the disease.

The fungal pathogens of *Fusarium* genus spread across grain cultivating areas all over the world, and are known to cause severe damage, particularly in areas with high rainfall between flowering and grain filling. When *Fusarium graminearum* is the causative agent, this disease is of primary concern because it does not only reduce the commercial values of the contaminated grains, in addition to yield losses, but because *Fusarium* infection can also lead to the accumulation of trichothecene mycotoxins in the grains thus threatening the health of human and livestock. Trichothecenes are major mycotoxin contaminants of cereals worldwide, causing feed refusal, vomiting, diarrhea and weight loss in non-ruminant animals and posing a health threat to other animals and humans when exposure levels are high. This threat has been exacerbated by the recent shift in the *F. graminearum* strains in the United States towards greater toxin production and vigor. Most frequently found mycotoxins are deoxynivalenol (DON, also known as vomitoxin) and zearalenone (ZEA). Deoxynivalenol in particular is a very dangerous toxin, causing gastrointestinal disorders accompanied by hemorrhagic conditions and the like in humans and animals that eat infected grains, leading to death in some cases. Since deoxynivalenol is generally stable against changes in pH and high temperature, detoxification can be very difficult. Therefore, grains contaminated beyond a certain level cannot be used in any form of brewing, processing, or livestock feed, and thus often need to be disposed of.

To date, various strategies have been deployed for controlling head blight in crop plants. Promising options include chemical measures, the development of resistant crop cultivars, and traditional practices of crop rotation and tillage of fields. Among these options, chemical pesticides can be somewhat effective in reducing head blight infestation, but residue concerns regarding the use of fungicides late in crop development, typically at flowering stages only a few weeks before harvest, lessen their attractiveness. Advances in developing resistant cultivars using traditional breeding and genetic engineering represent another disease control alternative are also occurring. Reported examples of genetic engineering advances include altering the production of a plant hormone or manipulating the plant hormone signaling pathway. In recent years, considerable advances in the area of traditional breeding have been made in understanding the genetic basis of resistance to head blight disease and a number of genes and quantitative trait loci (QTL) conferring resistance have been reported. However, progress in improving crop resistance to head blight disease has been slow, largely because of the difficulty of studying this disease. In fact, relatively little is currently understood about the mechanisms involved in resistance or susceptibility. In addition, the genetic diversity of *Fusarium* species, which are the predominant causative agents of the disease, often raises concerns regarding how durable the efficacy of chemical fungicides and resistant cultivars will be. As a result, practically all wheat cultivars currently in large-scale production remain vulnerable to infection.

In addition, although some success in controlling head blight disease can be expected by traditional practices such as plowing fields to bury crop residues infested with causative agent, e. g. *F. graminearum*, after harvest, conventional tillage of fields after harvesting is not compatible with the soil conservation practice of minimum tillage. Considering the potential of long distance inoculum dispersal and the diverse crops that can act as alternative hosts of the pathogens, crop rotation is often an untenable solution. In addition to the problem of pesticide residues in the environment, reports of pesticide resistance and instances of DON content increases in grain can also be concerns with their use. Further, costs and increasing concerns in the public and private sectors over pesticide residues in the environment and food product safety render this disease control alternative less attractive, and have led to requests for crop cultivation using as little pesticides as possible.

In summary, despite considerable advances in developing techniques to control head blight, reducing the impact of this devastating disease on grain production and quality remains an intractable problem. Therefore, identification and development of new head blight controlling techniques is essential in improving the production and quality of many cereal crops. These problems require urgent solution not only in United States, but also across the globe, including the Asia and Europe.

Biological control of head blight disease has attracted considerable interest since the mid 1990's. Biological control agents (BCAs), though currently very limited in number, could be an environmentally acceptable method for substantially decreasing the level of disease incited by pathogens such as *Fusarium*. Public acceptance, compatibility with other disease management measures, and durability are among favorable factors in support of developing strategies for biologically controlling head blight disease. Biological control agents could play an important role in organic cereal production. In conventional production, such agents may extend protection of spikes past the flowering stage after chemical fungicides can no longer be applied. To date, significant advances in the area of biological control have been achieved. For example, certain strains of spore-producing bacteria (such as *Bacillus* and *Pseudomonas* species) and yeasts (such as *Cryptococcus* species) show some promise for the control of head blight disease and the reduction of mycotoxin contamination. However, despite these and other advances, the need remains for improved microorganisms for use in the biological control of head blight disease. Although BCAs have become a more acceptable solution for plant pathogens and BCA products have been marketed to a greater extent than ever before, to date there have been few attempts to develop strategies and antagonistic microorganism for biologically controlling head blight disease. Furthermore, the life cycle of *Fusarium* spp. and other causative agents of head blight disease suggest that the pathogens can potentially be susceptible to biocontrol techniques using antagonistic microorganisms at different developmental stages. Thus, there is a need to identify new biological control agents, preferably with different modes of actions, as well as biocontrol methods that can help effectively prevent or suppress the development of head blight disease.

SUMMARY OF THE INVENTION

Compositions comprising microbiological strains and cultures are provided herein. Certain strains, cultures, and compositions thereof are useful for the control of head blight disease, for example, of various crop plants including wheat and other cereal plants. Biological control compositions, and methods of use thereof to prevent, inhibit or treat the development of plant pathogens or disease and for preserving plant yield, are also provided. Also provided are methods for the use of such compositions as biological control agents in combination with other agriculturally effective compounds or compositions for controlling harmful plant pathogens.

In one aspect, the present invention provides isolated microbial strains having suppressive activity against head blight disease. The microbial strains in accordance to this aspect of the present invention are selected from the group consisting of the genera *Microbacterium, Bacillus, Mycosphaerella*, and *Variovorax*. In some preferred embodiments, the microbial strains are selected from the group consisting of *Mycosphaerella* sp. strain SGI-010-H11 (deposited as NRRL 50471), *Microbacterium* sp. strain SGI-014-C06 (deposited as NRRL B-50470), *Microbacterium* sp. strain SGI-005-G08, *Variovorax* sp. strain SGI-014-G01 (deposited as NRRL B-50469), *Bacillus* sp. strain SGI-015-F03 (deposited as NRRL B-50760), *Bacillus* sp. strain SGI-015-H06 (deposited as NRRL B-50761), and pesticidally active variants of any thereof. The microbial strain in accordance to some other preferred embodiments can comprise a DNA sequence that exhibits at least 85% sequence identity to any one of the nucleotide sequences in the Sequence Listing. Further provided are biologically pure cultures and enriched cultures of the microbial strains disclosed herein.

Also provided in another aspect of the present invention are compositions that comprise a microbial strain of the invention or a culture thereof, and an agriculturally effective amount of a compound or composition selected from the group consisting of an acaricide, a bactericide, a fungicide, an insecticide, a microbicide, a nematicide, a pesticide, and a fertilizer. The compositions in some embodiments of this aspect may be prepared as a formulation selected from the group consisting of an emulsion, a colloid, a dust, a granule, a pellet, a powder, a spray, an emulsion, and a solution. In some other embodiments, the compositions may be provided with a carrier. In some preferred embodiment, the carrier is an agriculturally acceptable carrier. In some particularly preferred embodiment, the carrier is a plant seed. In other preferred embodiments, the composition is a seed coating formulation. Further provided in the present disclosure are seeds that are coated with a composition according to the present invention.

In another aspect of the present invention, there are provided methods for preventing, inhibiting or treating the development of a plant pathogen. The methods involve growing a microbial strain of the invention or a culture thereof in a growth medium or soil of a host plant prior to or concurrent with host plant growth in the growth medium or soil. In some preferred embodiments of this aspect, the plant pathogen causes head blight disease. In some particularly preferred embodiments, the plant pathogen is *Fusarium graminearum*.

In yet another aspect of the present invention, methods are provided for preventing, inhibiting or treating the development of head blight disease of a plant. The methods involve applying to the plant, or to the plant's surroundings, an effective amount of a microbial strain of the invention or a culture thereof. In one embodiment, such head blight disease is caused by the fungus *Fusarium graminearum*. In some embodiments of this aspect, the microbial strain or a culture thereof is applied to soil, a seed, a root, a flower, a leaf, a portion of the plant, or the whole plant. In a preferred embodiment, the plant is susceptible to *Fusarium graminearum*. In some other preferred embodiments, the plant is wheat plant, a corn plant, a barley plant, or an oat plant. In another preferred embodiment, the microbial strain of the present invention or a culture thereof is established as an endophyte on the plant.

Another further aspect of the invention provides non-naturally occurring plants. The non-naturally occurring plants are artificially infected with a microbial strain of the invention or a culture thereof. Further provided in some preferred embodiments of this aspect are seed, reproductive tissue, vegetative tissue, plant parts, and progeny of the non-naturally occurring plants.

Yet another aspect of the invention provides a method for preparing an agricultural composition. The method involves inoculating the microbial strain according to the present invention or a culture thereof into or onto a substratum and allowing it to grow at a temperature of 1-37° C. until obtaining a number of cells or spores of at least $10^2$-$10^3$ per milliliter or per gram.

These and other objects and features of the invention will become more fully apparent from the following detailed description of the invention and the claims.

DETAILED DESCRIPTION OF THE INVENTION

Some Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof.

The expressions "antagonistic microorganism" and "microbial antagonist" are used herein interchangeably in reference to a microorganism is intended to mean that the subject strain exhibits a degree of inhibition of head blight disease exceeding, at a statistically significant level, that of an untreated control.

Antibiotic: the term "antibiotic", as used herein, refers to any substance that is able to kill or inhibit the growth of a microorganism. Antibiotics may be produced by any one or more of the following: 1) a microorganism, 2) a synthetic process, or 3) a semisynthetic process. An antibiotic may be a microorganism that secretes a volatile organic compound. Furthermore, an antibiotic may be a volatile organic compound secreted by a microorganism.

Bactericidal: the term "bactericidal", as used herein, refers to the ability of a composition or substance to increase mortality or inhibit the growth rate of bacteria. Inhibition of the growth rate of bacteria can be commonly quantified as the reduction of viable bacterial cells over time.

Biological control: the term "biological control" and its abbreviated form "biocontrol", as used herein, is defined as control of a pathogen or insect or any other undesirable organism by the use of at least a second organism other than man. An example of a known mechanism of biological control is the use of microorganisms that control root rot by out-competing fungi for space on the surface of the root, or microorganisms that either inhibit the growth of or kill the pathogen. The "host plant" in the context of biological control is the plant that is susceptible to disease caused by the pathogen. In the context of isolation of an organism, such as a fungal species, from its natural environment, the "host plant" is a plant that supports the growth of the fungus, for example, a plant of a species the fungus is an endophyte of.

The term "cereal" as used herein is intended to refer to any cereal species that can be susceptible to head blight disease. Cereals reported to be susceptible include wheat, barley, oats, and triticale, though wheat and barley are the two crops in which this disease presents a significant economic problem.

An "effective amount" refers to an amount sufficient to affect beneficial or desired results. In terms of disease management, treatment, inhibition or protection, an effective amount is that amount sufficient to suppress, stabilize, reverse, slow or delay progression of the target infection or disease states. As such, the expression "an effective amount" is used herein in reference to that quantity of antagonist treatment which is necessary to obtain a reduction in the level of pathogen development and/or in the level of pathogenic disease relative to that occurring in an untreated control. Typically, an effective amount of a given antagonist treatment provides a reduction of at least 20%; or more typically, between 30 to 40%; more typically, between 50-60%; even more typically, between 70 to 80%; and even more typically, between 90 to 95%, relative to the level of disease and/or the level of pathogen development occurring in an untreated control under suitable conditions of treatment. An effective amount can be administered in one or more administrations. The actual rate of application of a liquid formulation will usually vary from a minimum of about $1\times10^3$ to about $1\times10^{10}$ viable cells/mL and preferably from about $1\times10^6$ to about $5\times10^9$ viable cells/mL. Under most conditions, the antagonistic microbial strains of the invention described in the Examples below, would be optimally effective at application rates in the range of about $1\times10^6$ to $1\times10^9$ viable cells/mL, assuming a mode of application which would achieve substantially uniform contact of at least about 50% of the plant tissues. If the antagonists are applied as a solid formulation, the rate of application should be controlled to result in a comparable number of viable cells per unit area of plant tissue surface as obtained by the aforementioned rates of liquid treatment. Typically, the biological control agents of the present invention are biologically effective when delivered at a concentration in excess of $10^6$ CFU/g (colony forming units per gram), preferably in excess of $10^7$ CFU/g, more preferably $10^8$ CFU/g, and most preferably at $10^9$ CFU/g.

Further, the expression "effective microbial antagonist" used herein in reference to a microorganism is intended to mean that the subject microbial strain exhibits a degree of inhibition of head blight disease exceeding, at a statistically significant level, that of an untreated control. Typically, an effective microbial antagonist has the ability to effect a reduction of at least 20%; or more typically, between 30 to 40%; more typically, between 50-60%; even more typically, between 70 to 80%; and even more typically, between 90 to 95%, relative to the level of disease and/or the level of pathogen development occurring in an untreated control under suitable conditions of treatment.

Composition: A "composition" is intended to mean a combination of active agent and at least another compound, carrier or composition, inert (for example, a detectable agent or label or liquid carrier) or active, such as a pesticide.

Isolated microbial strain, isolated culture, biologically pure culture, and enriched culture: As used herein, the term "isolated" as applied to a microorganism (e.g., bacterium or microfungus) refers to a microorganism which has been removed and/or purified from an environment in which it naturally occurs. As such, an "isolated strain" of a microbe as used herein is a strain that has been removed and/or purified from its natural milieu. Thus, an "isolated microorganism" does not include one residing in an environment in which it naturally occurs. Further, the term "isolated" does not necessarily reflect the extent to which the microbe has been purified. A "substantially pure culture" of the strain of microbe refers to a culture which contains substantially no other microbes than the desired strain or strains of microbe. In other words, a substantially pure culture of a strain of microbe is substantially free of other contaminants, which can include microbial contaminants as well as undesirable chemical contaminants. Further, as used herein, a "biologically pure" strain is intended to mean the strain separated from materials with which it is normally associated in nature. Note that a strain associated with other strains, or with compounds or materials that it is not normally found with in nature, is still defined as "biologically pure." A monoculture of a particular strain is, of course, "biologically pure." As used herein, the term "enriched culture" of an isolated microbial strain refers to a microbial culture that contains more than 50%, 60%, 70%, 80%, 90%, or 95% of the isolated strain.

As used herein, an "endophyte" is an endosymbiont that lives within a plant for at least part of its life without causing apparent disease. Endophytes may be transmitted either vertically (directly from parent to offspring) or horizontally (from individual to unrelated individual). Vertically-transmitted fungal endophytes are typically asexual and transmit from the maternal plant to offspring via fungal hyphae penetrating the host's seeds. Bacterial endophytes can also be transferred vertically from seeds to seedlings (Ferreira et al., 2008). Conversely, horizontally-transmitted endophytes are typically sexual, and transmit via spores that can be spread by wind and/or insect vectors. Endophytes of crop plants have been receiving considerable attention with respect to their ability to control both disease and insect infestation, as well as promoting plant growth.

Functionally comparable protein: The phrase "functionally comparable protein" as used herein describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs, paralogs and analogs are considered to be functionally comparable. In addition, functionally comparable proteins generally share at least one biochemical and/or phenotypic activity. Functionally comparable proteins will give rise to the same characteristic to a similar, but not necessarily the same, degree. Typically, functionally comparable proteins give the same characteristics where the quantitative measurement due to one of the comparables is at least 20% of the other; more typically, between 30 to 40%; more typically, between 50-60%; even more typically, between 70 to 80%; even more typically, between 90 to 95%; even more typically, between 98 to 100% of the other.

Fungicidal: As used herein, "fungicidal" refers to the ability of a composition or substance to decrease the rate of growth of fungi or to increase the mortality of fungi.

*Fusarium* fungus: For purposes of this invention it is understood that the use of term *Fusarium* fungus is intended to include both the sexual (teleomorphic) stage of this organism and also the asexual (anamorphic) stage, also referred to as the perfect and imperfect fungal stages, respectively. For example, the anamorphic stage of *Fusarium graminearum* is *Gibberella zeae*, a causative agent of head blight disease. This disease typically occurs when the flower or seed head becomes inoculated with conidia produced by the imperfect form or ascospores produced by the perfect form of this fungus.

Mutant: As used herein, the term "mutant" or "variant" in reference to a microorganism refers to a modification of the parental strain in which the desired biological activity is similar to that expressed by the parental strain. For example, in the case of *Microbacterium* the "parental strain" is defined herein as the original *Microbacterium* strain before mutagenesis. Mutants or variants may occur in nature without the intervention of man. They also are obtainable by treatment with or by a variety of methods and compositions known to those of skill in the art. For example, a parental strain may be treated with a chemical such as N-methyl-N'-nitro-N-nitrosoguanidine, ethylmethanesulfone, or by irradiation using gamma, X-ray, or UV-irradiation, or by other means well known to those practiced in the art.

Nematicidal: The term "nematicidal", as used herein, refers to the ability of a substance or composition to increase mortality or inhibit the growth rate of nematodes.

Pathogen: The term "pathogen" as used herein refers to an organism such as an alga, an arachnid, a bacterium, a fungus, an insect, a nematode, a parasitic plant, yeast, a protozoan, or a virus capable of producing a disease in a plant or animal. The term "phytopathogen" as used herein refers to a pathogenic organism that infects a plant.

Percentage of percent identity: "percentage of sequence identity", as used herein, is determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (1981) Add. APL. Math. 2:482, by the global homology alignment algorithm of Needleman and Wunsch (*J. Mol. Biol.* 48:443, 1970), by the search for similarity method of Pearson and Lipman (*Proc. Natl. Acad. Sci. USA* 85: 2444, 1988), by heuristic implementations of these algorithms (NCBI BLAST, WU-BLAST, BLAT, SIM, BLASTZ), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, preferably at least 70%, preferably at least 80%, more preferably at least 85%, more preferably at least 90%, even more preferably at least 95%, and most preferably at least 96%, 97%, 98% or 99% sequence identity compared to a reference sequence using the programs.

Query nucleic acid and amino acid sequences can be searched against subject nucleic acid or amino acid sequences residing in public or proprietary databases. Such searches can be done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Typically the following parameters for NCBI BLAST can be used: Filter options set to "default", the Comparison Matrix set to "BLOSUM62", the Gap Costs set to "Existence: 11, Extension: 1", the Word Size set to 3, the Expect (E threshold) set to 1 e-3, and the minimum length of the local alignment set to 50% of the query sequence length. Sequence identity and similarity may also be determined using GenomeQuest™ software (Gene-IT, Worcester Mass. USA).

The term "pesticidal", as used herein, refers to the ability of a substance or composition to decrease the rate of growth of a pest, i.e., an undesired organism, or to increase the mortality of a pest.

By "suppressive activity" of a biological control agent against a phytopathogen is meant the ability of the agent to suppress, inhibit, stabilize, reverse, slow, or delay the development of the pathogen itself, or the progression of the infection or disease states caused by the pathogen.

Variant: A "variant", as used herein in reference to a microorganism, is a strain having identifying characteristics of the species to which it belongs, while having at least one nucleotide sequence variation or identifiably different trait with respect to the parental strain, where the trait is genetically based (heritable). For example, for a *Microbacterium* sp. SGI-SGI-014-C06 strain having fungicidal activity, identifiable traits include 1) the ability to suppress the growth of *Fusarium graminearum* and its teleomorph *Gibberella zeae*; 2) the ability to suppress the development of head blight disease; 3) having housekeeping genes with greater than 95%, greater than 96%, greater than 97%, greater than 98%, or greater than 99% sequence identity to the housekeeping genes of *Microbacterium* sp. SGI-014-C06 can be used to confirm a variant as *Microbacterium* sp. SGI-014-C06.

For nucleic acids and polypeptides, the term "variant" is used herein to denote a polypeptide, protein or polynucleotide molecule with some differences, generated synthetically or naturally, in their amino acid or nucleic acid sequences as compared to a reference polypeptide or polynucleotide, respectively. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation, phosphorylation, etc.).

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents forms part of the common general knowledge in the art.

Methods for Taxonomic Identification

Microorganisms can often be distinguished based on direct microscopic analysis (do all of the cells in a sample look the same on examination), staining characteristics, simple molecular analysis (such as a simply restriction fragment length polymorphism (RFLP) determination), and so forth. In addition to the illustrative examples of such taxonomic analysis techniques as described at Examples 2-3 of the present disclosure, taxonomic identification of a microorganism can involve up to several different levels of analysis, and each analysis can be based on a different characteristic of the organism. Such taxonomic analyses can include nucleic acid-based analysis (e.g., analysis of individual specific genes, either as to their presence or their exact sequence, or expression of a particular gene or a family of genes), protein-based analysis (e.g., at a functional level using direct or indirect enzyme assays, or at a structural level using immuno-detection techniques), and so forth.

a. Nucleic Acid-Based Analysis:

One of ordinary skill in the art will appreciate that a wide variety of nucleic acid-based techniques are known and can be useful in obtaining the taxonomic identification of a given microorganism. These techniques can be used to identify cells by gene sequence or to identify cells that have particular genes or gene families. Common gene families useful for taxonomic studies include 16S gene family, actin gene family, and recombinase A (recA) gene family. These methods typically include amplifying and sequencing genes from very small numbers of cells, and therefore often overcome the problems of concentrating cells and their DNA from dilute suspensions. The term "nucleic acid amplification" generally refers to techniques that increase the number of copies of a nucleic acid molecule in a sample or specimen. Techniques useful for nucleic acid amplification are well known in the art. An example of nucleic acid amplification is the polymerase chain reaction (PCR), in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. Other examples of in vitro amplification techniques include strand displacement amplification; transcription-free isothermal amplification; repair chain reaction amplification; ligase chain reaction; gap filling ligase chain reaction amplification; coupled ligase detection and PCR; and RNA transcription-free amplification.

In addition to the illustrative example primers provided herein, see, e.g. Examples 2-3 and the Sequence Listing, primers have also been designed routinely, and new ones are continually being designed, for individual species or phylogenetic groups of microorganisms. Such narrowly targeted primers can be used with the methods described herein to screen and/or identify specifically only the microorganisms of interest.

Methods for preparing and using nucleic acid primers are described, for example, in Sambrook et al. (In Molecular Cloning: A Laboratory Manual, CSHL, New York, 1989), Ausubel et al. (ed.) (In Current Protocols in Molecular Biology, John Wiley & Sons, New York, 1998). Amplification primer pairs can be derived from a known sequence, for example, by using computer programs intended for that purpose such as Primer (Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of an rRNA-encoding nucleotide or flanking region thereof will anneal to a target sequence with a higher specificity than a corresponding primer of only 15 nucleotides. Thus, in order to obtain greater specificity, probes and primers can be selected that comprise at least 20, 25, 30, 35, 40, 45, 50 or more consecutive nucleotides of a target nucleotide sequence such as the 16S rRNA.

Common techniques for the preparation of nucleic acids useful for nucleic acid applications (e.g., PCR) include phenol/chloroform extraction or use of one of the many DNA extraction kits that are available on the market. Another way that DNA can be amplified is by adding cells directly to the nucleic acid amplification reaction mix and relying on the denaturation step of the amplification to lyse the cells and release the DNA.

The product of nucleic acid amplification reactions may be further characterized by one or more of the standard techniques that are well known in the art, including electrophoresis, restriction endonuclease cleavage patterns, oligonucleotide hybridization or ligation, and/or nucleic acid sequencing. When in hybridization techniques are used for cell identification purposes, a variety of probe labeling methods can be useful, including fluorescent labeling, radioactive labeling and non-radioactive labeling. When nucleic acid sequencing techniques are used, homology search for the nucleotide sequence of the amplified nucleic acid molecules can be conducted using various databases of known sequences, including but not limited to DDBJ/GenBank/EMBL databases.

b. Protein-Based Analysis:

In addition to analysis of nucleic acids, microorganisms can be taxonomically characterized and identified based on the presence (or absence) of specific proteins directly. Such analysis can be based on the activity of the specified protein, e.g., through an enzyme assay or by the response of a co-cultured organisms, or by the mere presence of the specified protein (which can for instance be determined using immunologic methods, such as in situ immunofluorescent antibody staining).

Enzyme assays: By way of example, fluorescent or chromogenic substrate analogs can be included into the growth media (e.g., microtiter plate cultures), followed by incubation and screening for reaction products, thereby identifying cultures on a basis of their enzymatic activities.

Co-cultivation response: In some embodiments of the present invention, the activity of an enzyme carried by a microbial isolate can be assayed based on the response (or degree of response) of a co-cultured organism (such as a reporter organism).

A variety of methods can also be used for identifying microorganisms selected and isolated from a source environment by binding at least one antibody or antibody-derived molecule to a molecule, or more particularly an epitope of a molecule, of the microorganism.

Anti-microorganism protein antibodies may be produced using standard procedures described in a number of texts, including Harlow and Lane (Antibodies, A Laboratory Manual, CSHL, New York, 1988). The determination that a particular agent binds substantially only to a protein of the desired microorganism may readily be made by using or adapting routine procedures. One suitable in vitro assay makes use of the Western blotting procedure (described in many standard texts, including Harlow and Lane (Antibodies, A Laboratory Manual, CSHL, New York, 1988)).

Shorter fragments of antibodies (antibody-derived molecules, for instance, FAbs, Fvs, and single-chain Fvs (SCFvs)) can also serve as specific binding agents. Methods of making these fragments are routine.

Detection of antibodies that bind to cells on an array of this invention can be carried out using standard techniques, for instance ELISA assays that provide a detectable signal, for instance a fluorescent or luminescent signal.

Isolated Cultures of the Invention

As described in more details in the Examples section of the present disclosure, Applicants have discovered several agriculturally beneficial novel microorganisms, for example, effective suppressors of head blight disease. Particularly, these novel antagonistic microorganisms are effective for reduction of head blight severity and for inhibition of the growth of *Fusarium graminearum*, a primary causative agent of head blight disease in wheat. The microbial antagonists were identified from a pool of approximately 5,000 microbial strains obtained from wild plant samples collected from several locations in the United States. Initial selection of antagonistic microorganism was based on the ability of the microorganisms to suppress the development of *F. graminearum* pathogen and that of its teleomorph *Gibberella zeae* in an in vitro antagonism assay. Selected microbial antagonists were then bio-assayed in a greenhouse study on wheat seedlings, which involved inoculation of the seedlings with the microbial strains, followed by repeated inoculations of *F. graminearum* spores, for the ability of the microbial strains to reduce the severity of fungal infestation and for their ability to preserve seed yield. The antagonistic microorganisms selected in this manner were found to be effective in reducing the severity of head blight in greenhouse trials.

Taxonomic analysis further determined that each of the antagonistic microorganisms described in the present disclosure are closely related either the bacterial genus *Microbacterium*, the bacterial genus *Bacillus*, the bacterial genus *Variovorax*, or the fungus genus *Mycosphaerella*.

The genus *Microbacterium*, the type genus of the family Microbacteriaceae, is generally considered to accommodate Gram-positive, non-spore forming, rod-shaped bacteria that were originally isolated during early studies on lactic acid-producing bacteria. Members of the genus *Microbacterium* are originally characterized largely by their marked heat resistance, presence in dairies, and production of small amounts of L(+) lactic acid from glucose. In contrast to other genera of the family Microbacteriaceae in which species are characterized by a coherent peptidoglycan type, species of *Microbacterium* possess ornithine or lysine either in the inter-peptide bridge or at position 3 of B-type peptidoglycan. In other chemotaxonomic properties, such as isoprenoid quinones (MK-11, MK-12, MK-13), polar lipids, fatty acids and base composition of DNA, members of the genus exhibit the usual range of diversity found in other genera of Microbacteriaceae. Two bacterial genera *Microbacterium* and *Aureobacterium* can be united according to some taxonomy studies. To date, members of the genus *Microbacterium* comprise at least 33 species, which have been isolated from a broad range of habitats, including soil, dairy products, plant galls, insects or clinical specimens. Various aspects of their ecology, phylogeny, taxonomy, culture methods, and long-term preservation conditions have recently been summarized by Evtushenko and Takeuchi (2006). One of skill in the art will readily appreciate that microorganism of the genus *Microbacterium* can be taxonomically identified largely by any of the taxonomic identification techniques described above, including the chemotaxonomic analysis of the cell wall peptidoglycan and comparative 16S rDNA sequence analysis as described in Evtushenko and Takeuchi (2006) and references cited therein, as well as in those described in Examples 2-3 of the present disclosure. As discussed in detail below, to date several naturally occurring microorganisms have been reported as having antagonistic activity against head blight disease. However, there are no reports prior to the present invention that describe a microorganism of the genus *Mycobacterium* having such antagonistic activity. Further, prior to the present invention, the present inventors were not aware of any methods or processes of using a bacterial strain of the genus *Mycobacterium* as biocontrol agent in preventing, inhibiting or treating the development of a causative pathogen of head blight disease.

The genus *Bacillus* is a genus of Gram-positive/variable, spore-forming, rod-shaped bacteria. Similarly to other genera associated with the early history of microbiology, such as *Pseudomonas* or *Vibrio*, nearly 266 species members of the *Bacillus* genus are found ubiquitously, and it is widely considered to be one of the genera with the largest 16S diversity and environmental diversity. *Bacillus* species can be obligate aerobes or facultative anaerobes, and test positive for the enzyme catalase. Ubiquitous in nature, *Bacillus* includes both free-living and pathogenic species. Under stressful environmental conditions, the cells produce oval endospores that can stay dormant for extended periods. These characteristics originally defined the genus, but not all such species are closely related, and many have been moved to other genera. In fact, several studies have tried to reconstruct the phylogeny of the genus. The *Bacillus*-specific study with the most diversity covered is by Xu and Cote [*Intl. J. of Syst. Evol. Microbiol.* 53 (3): 695-704; 2003], using 16S and the ITS region, where they divide the genus into 10 groups, which includes the nested genera *Paenibacillus, Brevibacillus, Geobacillus, Marinibacillus* and *Virgibacillus*. However, according to more recent studies, the genus *Bacillus* contains a very large number of nested taxa and especially in both 16S and 23S it is considered to be paraphyletic to Lactobacillales (*Lactobacillus, Streptococcus, Staphylococcus, Listeria*, etc.), due to *Bacillus coahuilensis* and others (see, e.g., Yarda et al., Syst. Appl. Microbiol. 31 (4): 241-250, 2008; Yarda et al., Syst. Appl. Microbiol. 33 (6): 291-299, 2010]. One particular Glade, formed by *B. anthracis, B. cereus, B. mycoides, B. pseudomycoides, B. thuringiensis* and *B. weihenstephanensis* under current classification standards, should be a single species (within 97% 16S identity), but due to medical reasons, they are considered separate species. In addition to the taxonomy analysis methods described at Examples 2-3 of the present disclosure, the phylogenetic and taxonomic analyses of *Bacillus* species can be performed by a variety of techniques, including those discussed in details in Xu and Cote, 2003; Yarda et al., 2008; Yarda et al., 2010.

The genus *Variovorax* was originally created by reclassification of *Alcaligenes paradoxus* as *Variovorax paradoxus* (Willems et al., 1991), which is widely consider as the type species of this genus. *V. paradoxus* has been extensively studied as a model for novel biodegradation agents, as well as microbe/microbe and microbe/plant interactions. Other species include *V. dokdonensis, V. soli* (Kim et al., 2006), and *V. boronicumulans* (Miwa et al., 2008). *Variovorax* species are catabolically very diverse and engage in mutually beneficial interactions with other bacterial species in many biodegradations, and therefore possess ecological importance and high application potential. For example, a soil methanotroph, only when co-cultured together with a *V. paradoxus* strain, exhibits high affinity for methane (a potent greenhouse gas), and this trait is not usually observed in laboratory cultures. Similarly, a close relative of *Variovorax* has been found to be the central, non-photosynthetic partner within the phototrophic consortium "*Chlorochromatium aggregatum*." Some species of the genus *Variovorax* also have the ability to interfere with the communication of other bacteria. Some yet other species of the genus *Variovorax* can intimately interact with other biota (e.g., plants) in various ecosystems. Moreover, some *Variovorax* species, residing in the area just outside plant roots and/or inside a plant, have been reported for being capable of promoting plant growth via the reduction of ethylene levels, the repression of quorum-sensing-controlled pathogenesis, and the increase of resistance to heavy metals, which greatly benefits phytoremediation. In addition to the taxonomy analysis methods described at Examples 2-3 of the present disclosure, the phylogenetic and taxonomic analyses of *Variovorax* species can be performed by a variety of techniques, including those discussed in details elsewhere herein.

*Mycosphaerella* is a very large fungus genus, with over 2,000 species names and at least 500 species associated with more than 40 anamorph genera (especially *Cercospora, Pseudocercospora, Septoria, Ramularia*, etc.). In addition, several thousand anamorphs lack telomorphs. The genus of *Mycosphaerella* includes species that are pathogens, saprobes, endophytes, or mutualistic associations. Various aspects of their ecology, phylogeny, taxonomy, culture methods, and long-term preservation conditions have recently been reported (see, e.g. Crous et al., *Persoonia*, 23:119-146, 2009). One of skill in the art will readily appreciate that microorganism of the genus *Mycosphaerella* can be taxonomically identified by any of the taxonomic techniques described above, or a combination thereof. Most common techniques include comparative sequence analyses using 16S rDNA sequences and the internal transcribed spacer regions as described in, for example, Crous et al., *Studies in Mycology*, 55:235-253, 2006; Crous et al., 2009, supra; Goodwin et al., *Phytopathology* 91: 648-658, 2001; and those described in Examples 2-3 of the present disclosure.

Deposit of Biological Material

Purified cultures of microbial strains identified as having suppressive activity against head blight disease were deposited in the Agricultural Research Service Culture Collection located at 1815 N. University Street, Peoria, Ill. 61604, USA (NRRL) in accordance with and accepted under the Budapest Treaty for the purpose of patent procedure and the regulations thereunder (Budapest Treaty). Accession numbers and the dates of deposit for these deposits are as follows:

| SGI Strain ID | Accession No | Deposit Date | Provisional Taxonomy |
|---|---|---|---|
| SGI-010-H11 | NRRL 50471 | Feb. 18, 2011 | *Mycosphaerella* sp. |
| SGI-014-C06 | NRRL B-50470 | Feb. 18, 2011 | *Microbacterium* sp. |
| SGI-014-G01 | NRRL B-50469 | Feb. 18, 2011 | *Variovorax* sp. |
| SGI-015-F03 | NRRL B-50760 | Jun. 21, 2012 | *Bacillus* sp. |
| SGI-015-H06 | NRRL B-50761 | Jun. 21, 2012 | *Bacillus* sp. |

The microbial strains have been deposited under conditions that ensure that access to the culture will be available during the pendency of this patent application to one determined by the Commissioner of Patents and Trademarks to be entitled thereto under 37 C.F.R. § 1.14 and 35 U.S.C. § 122.

The deposits represent substantially pure cultures of the deposited strains. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Preferred microorganisms of the present invention have all of the identifying characteristics of the deposited strains and, in particular, the identifying characteristics of being able to suppress the development of head blight disease as described herein, and as being able to suppress the development of *Fusarium graminearum* pathogen and its teleomorph *Gibberella zeae* as described herein. In particular, the preferred microorganisms of the present invention refer to the deposited microorganisms as described above, and mutants thereof Microbiological Compositions The microbiological compositions of the present invention that comprise isolated microbial strains or cultures thereof can be in a variety of forms, including, but not limited to, still cultures, whole cultures, stored stocks of cells, mycelium and/or hyphae (particularly glycerol stocks), agar strips, stored agar plugs in glycerol/water, freeze dried stocks, and dried stocks such as lyophilisate or mycelia dried onto filter paper or grain seeds. As defined elsewhere herein, "isolated culture" or grammatical equivalents as used in this disclosure and in the art is understood to mean that the referred to culture is a culture fluid, pellet, scraping, dried sample, lyophilate, or section (for example, hyphae or mycelia); or a support, container, or medium such as a plate, paper, filter, matrix, straw, pipette or pipette tip, fiber, needle, gel, swab, tube, vial, particle, etc. that contains a single type of organism. In the present invention, an isolated culture of a microbial antagonist is a culture fluid or a scraping, pellet, dried preparation, lyophilate, or section of the microorganism, or a support, container, or medium that contains the microorganism, in the absence of other organisms.

The present disclosure further provides compositions that contain at least one isolated microbial strains or cultures thereof of the present invention and a carrier. The carrier may be any one or more of a number of carriers that confer a variety of properties, such as increased stability, wettability, dispersability, etc. Wetting agents such as natural or synthetic surfactants, which can be nonionic or ionic surfactants, or a combination thereof can be included in a composition of the invention. Water-in-oil emulsions can also be used to formulate a composition that includes at least one isolated microorganism of the present invention (see, for example, U.S. Pat. No. 7,485,451, incorporated by reference herein). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products (e.g., ground grain or beans, broth or flour derived from grain or beans), starch, sugar, or oil. The carrier may be an agricultural carrier. In certain preferred embodiments, the carrier is a seed, and the composition may be applied or coated onto the seed or allowed to saturate the seed.

In some embodiments, the agricultural carrier may be soil or plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant parts, sugar cane bagasse, hulls or stalks from grain processing, ground plant material (e.g. "yard waste") or wood from building site refuse, sawdust or small fibers from recycling of paper, fabric, or wood. Other suitable formulations will be known to those skilled in the art.

In the liquid form, e.g. solutions or suspensions, the microorganisms may be mixed or suspended in water or in aqueous solutions. Suitable liquid diluents or carriers include water, aqueous solutions, petroleum distillates, or other liquid carriers.

Solid compositions can be prepared by dispersing the antagonist microorganisms in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

In a preferred embodiment, the compositions contemplated herein prevent attack by head blight disease upon plants, particularly cereal plants, such as wheat, barley, oat, and corn and, when used in sufficient amounts, to act as microbial antagonists. These compositions, similarly to other biocontrol agents, have a high margin of safety because they typically do not burn or injury the plant.

As described in great detail throughout the present disclosure, control of head blight disease may be effected by application of one or more of the microbiological compositions of the present invention to a host plant or parts of the host plant. The compositions can be applied in an amount effective to reduce the level of head blight relative to that in an untreated control. The active constituents are used in a concentration sufficient to inhibit plant pathogen development of the targeted plant pathogen when applied to the cereal plant. As will be apparent to a skilled person in the art, effective concentrations may vary depending upon such factors as: (a) the type of the plant or agricultural commodity; (b) the physiological condition of the plant or agricultural commodity; (c) the concentration of pathogens affecting the plant or agricultural commodity; (d) the type of disease injury on the plant or agricultural commodity; (e) weather conditions (e.g. temperature, humidity); and (f) the stage of plant disease. According to the invention, typical concentrations are those higher than $1 \times 10^2$ CFU/mL of carrier. Preferred concentrations range from about $1 \times 10^4$ to about $1 \times 10^9$ CFU/mL, such as the concentrations ranging from $1 \times 10^6$ to $1 \times 10^8$ CFU/mL. More preferred concentrations are those of from about 35 to about 150 mg dry microbial mass per gram of carrier (dry formulation) or per milliliter of carrier (liquid composition). In solid formulations, the rate of application should be controlled to result in a comparable number of viable cells per unit area of plant tissue surface as obtained by the aforementioned rates of liquid treatment. Typically, the biological control agents of the present invention are biologically effective when delivered at a concentration in excess of $10^6$ CFU/g (colony forming units per gram), preferably in excess of $10^7$ CFU/g, more preferably $10^8$ CFU/g, and most preferably at $10^9$ CFU/g.

In some embodiments, the amount of one or more of the biological control agents in the microbial compositions of the present invention can vary depending on the final formulation as well as size or type of the plant or seed utilized. Preferably, the one or more biological control agents in the microbial compositions are present in about 2% w/w/ to about 80% w/w of the entire formulation. More preferable, the one or more biological control agents employed in the compositions is about 5% w/w to about 65% w/w and most preferably about 10% w/w to about 60% w/w by weight of the entire formulation.

As it will be appreciated by those skilled in the art, the microbiological compositions of the invention may be applied to the wheat plant or other cereals using a variety of conventional methods such as dusting, coating, injecting, rubbing, rolling, dipping, spraying, or brushing, or any other appropriate technique which does not significantly injure the wheat plant or other cereals to be treated. Particularly preferred is the spray method.

Typically, the compositions of the invention are chemically inert; hence they are compatible with substantially any other constituents of the spray schedule. They may also be used in combination with biologically compatible pesticidal active agents as for example, herbicides, nematicides, fungicides, insecticides, and the like. They can also be used in combination with plant growth affecting substances, such as fertilizers, plant growth regulators, and the like, provided that such compounds or substances are biologically compatible.

When used as pesticides or fungicide in their commercially available formulations and in the use forms, prepared from these formulations, the active microbial antagonists and compositions according to the present invention can furthermore be present in the form of a mixture with synergists. Synergists are compounds by which the activity of the active compositions is increased without it being necessary for the synergist added to be active itself.

When used as pesticides in their commercially available formulations and in the use forms, prepared from these formulations, the active microbial antagonists and compositions according to the invention can furthermore be present in the form of a mixture with inhibitors which reduce the degradation of the active compositions after application in the habitat of the plant, on the surface of parts of plants or in plant tissues.

The active microbial antagonists and compositions according to the invention, as such or in their formulations, can also be used as a mixture with known acaricides, bactericides, fungicides, insecticides, microbicides, nematicides, pesticides, or combinations thereof, for example in order to widen the spectrum of action or to prevent the development of resistances in this way. In many cases, synergistic effects result, i.e. the activity of the mixture can exceed the activity of the individual components. A mixture with other known active compounds, such as fertilizers, growth regulators, safeners and/or semiochemicals is also contemplated.

In a preferred embodiment of the present invention, the compositions may further include at least one chemical or biological pesticide. The amount of at least one chemical or biological pesticide employed in the compositions can vary depending on the final formulation as well as the size of the plant and seed to be treated. Preferably, the at least one chemical or biological pesticide employed is about 0.1% w/w to about 80% w/w based on the entire formulation. More preferably, the at least one chemical or biological pesticide is present in an amount of about 1% w/w to about 60% w/w and most preferably about 10% w/w to about 50% w/w.

A variety of pesticides is apparent to one of skill in the art and may be used. Exemplary chemical pesticides include those in the carbamate, organophosphate, organochlorine, and prethroid classes. Also included are chemical control agents such as, but not limited to, benomyl, borax, captafol, captan, chorothalonil, formulations containing copper; formulations containing dichlone, dicloran, iodine, zinc; fungicides that inhibit ergosterol biosynthesis such as but not limited to blastididin, cymoxanil, fenarimol, flusilazole, folpet, imazalil, ipordione, maneb, manocozeb, metalaxyl, oxycarboxin, myclobutanil, oxytetracycline, PCNB, pentachlorophenol, prochloraz, propiconazole, quinomethionate, sodium aresenite, sodium DNOC, sodium hypochlorite, sodium phenylphenate, streptomycin, sulfur, tebuconazole, terbutrazole, thiabendazolel, thiophanate-methyl, triadimefon, tricyclazole, triforine, validimycin, vinclozolin, zineb, and ziram. A variety of insecticidal compounds can be useful for the compositions of the invention, including but not limited to those cited in U.S. Pat. Appl. No. 20110033432A1.

The microbiological compositions of the present invention preferably include at least one biological pesticide. Exemplary biological pesticides that are suitable for use herein and can be included in a microbiological composition according to the present invention for preventing a plant pathogenic disease include microbes, animals, bacteria, fungi, genetic material, plant, and natural products of living organisms. In these compositions, the microorganism of the present invention is isolated prior to formulation with an additional organism. For example, microbes such as but not limited to species of *Ampelomyces, Aureobasidium, Bacillus, Beauveria, Candida, Chaetomium, Cordyceps, Cryptococcus, Dabaryomyces, Erwinia, Exophilia, Gliocladium, Mariannaea, Paecilomyces, Paenibacillus, Pantoea, Pichia, Pseudomonas, Sporobolomyces, Talaromyces*, and *Trichoderma* can be provided in a composition with the antagonistic microorganisms of the present invention, with fungal strains of the *Muscodor* genus being particularly preferred. Use of the microbiological compositions according to the present invention in combination with the microbial antagonists disclosed in U.S. Pat. Nos. 7,518,040; 7,601,346; 6,312,940 is also particularly preferred.

Examples of fungi that can be combined with microbial antagonists and compositions of the present invention in a composition include, without limitation, *Muscodor* species, *Aschersonia aleyrodis, Beauveria bassiana* ("white muscarine"), *Beauveria brongniartii, Chladosporium herbarum, Cordyceps clavulata, Cordyceps entomorrhiza, Cordyceps facis, Cordyceps gracilis, Cordyceps melolanthae, Cordyceps militaris, Cordyceps myrmecophila, Cordyceps ravenelii, Cordyceps sinensis, Cordyceps sphecocephala, Cordyceps subsessilis, Cordyceps unilateralis, Cordyceps variabilis, Cordyceps washingtonensis, Culicinomyces clavosporus, Entomophaga grylli, Entomophaga maimaiga, Entomophaga muscae, Entomophaga praxibulli, Entomophthora plutellae, Fusarium lateritium, Hirsutella citriformis, Hirsutella thompsoni, Metarhizium anisopliae* ("green muscarine"), *Metarhizium flaviride, Muscodor albus, Neozygitesfloridana, Nomuraea rileyi, Paecilomyces farinosus, Paecilomyces fumosoroseus, Pandora neoaphidis, Tolypocladium cylindrosporum, Verticillium lecanii, Zoophthora radicans*, and mycorrhizal species such as *Laccaria bicolor*. Other mycopesticidal species will be apparent to those skilled in the art.

The present invention also provides methods of treating a plant by application of any of a variety of customary formulations in an effective amount to either the soil (i.e., in-furrow), a portion of the plant (i.e., drench) or on the seed before planting (i.e., seed coating or dressing). Customary formulations include solutions, emulsifiable concentrate, wettable powders, suspension concentrate, soluble powders, granules, suspension-emulsion concentrate, natural and synthetic materials impregnated with active compound, and very fine control release capsules in polymeric substances. In certain embodiments of the present invention, the biological control compositions are formulated in powders that are available in either a ready-to-use formulation or are mixed together at the time of use. In either embodiment, the powder may be admixed with the soil prior to or at the time of planting. In an alternative embodiment, one or both of either the biological control agent or insect control agent is a liquid formulation that is mixed together at the time of treating. One of ordinary skill in the art understands that an effective amount of the inventive compositions depends on the final formulation of the composition as well as the size of the plant or the size of the seed to be treated.

Depending on the final formulation and method of application, one or more suitable additives can also be introduced to the compositions of the present invention. Adhesives such as carboxymethylcellulose and natural and synthetic polymers in the form of powders, granules or latexes, such as gum arabic, chitin, polyvinyl alcohol and polyvinyl acetate, as well as natural phospholipids, such as cephalins and lecithins, and synthetic phospholipids, can be added to the present compositions.

In a preferred embodiment, the microbiological compositions are formulated in a single, stable solution, or emulsion, or suspension. For solutions, the active chemical compounds (i.e., the pest control agents) are typically dissolved in solvents before the biological control agent is added. Suitable liquid solvents include petroleum based aromatics, such as xylene, toluene or alkylnaphthalenes, aliphatic hydrocarbons, such as cyclohexane or paraffins, for example petroleum fractions, mineral and vegetable oils, alcohols, such as butanol or glycol as well as their ethers and esters, ketones, such as methyl ethyl ketone, methyl isobutyl ketone or cyclohexanone, strongly polar solvents, such as dimethylformamide and dimethyl sulphoxide. For emulsion or suspension, the liquid medium is water. In one embodiment, the chemical control agent and biological control agent are suspended in separate liquids and mixed at the time of application. In a preferred embodiment of suspension, the insect control agent and biologic are combined in a ready-to-use formulation that exhibits a shelf-life of at least two years. In use, the liquid can be sprayed or can be applied foliarly as an atomized spray or in-furrow at the time of planting the crop. The liquid composition can be introduced to the soil before germination of the seed or directly to the soil in contact with the roots by utilizing a variety of techniques known in the art including, but not limited to, drip irrigation, sprinklers, soil injection or soil drenching.

Optionally, stabilizers and buffers can be added, including alkaline and alkaline earth metal salts and organic acids, such as citric acid and ascorbic acid, inorganic acids, such as hydrochloric acid or sulfuric acid. Biocides can also be added and can include formaldehydes or formaldehyde-releasing agents and derivatives of benzoic acid, such as p-hydroxybenzoic acid.

Seed Coating Formulations

In some particularly preferred embodiments, the biocontrol compositions of the present invention are formulated as a seed treatment. The seed treatment preferably comprises at least one insect control agent and at least one biological control agent. It is contemplated that the seeds can be substantially uniformly coated with one or more layers of the biocontrol compositions disclosed herein using conventional methods of mixing, spraying or a combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists or a combination thereof. Liquid seed treatments such as those of the present invention can be applied via either a spinning "atomizer" disk or a spray nozzle which evenly distributes the seed treatment onto the seed as it moves though the spray pattern. Preferably, the seed is then mixed or tumbled for an additional period of time to achieve additional treatment distribution and drying. The seeds can be primed or unprimed before coating with the inventive compositions to increase the uniformity of germination and emergence. In an alternative embodiment, a dry powder formulation can be metered onto the moving seed and allowed to mix until completely distributed.

Another aspect of the invention provides seeds treated with the subject microbiological compositions. One embodiment provides seeds having at least part of the surface area coated with a microbiological composition according to the present invention. In a specific embodiment, the microorganism-treated seeds have a spore concentration or microbial cell concentration from about $10^6$ to about $10^9$ per seed. The seeds may also have more spores or microbial cells per seed, such as, for example $10^{10}$, $10^{11}$ or $10^{12}$ spores per seed. The microbial spores and/or cells can be coated freely onto the seeds or, preferably, they can be formulated in a liquid or solid composition before being coated onto the seeds. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid biocontrol compositions of the present invention further contain functional agents capable of protecting seeds from the harmful effects of selective herbicides such as activated carbon, nutrients (fertilizers), and other agents capable of improving the germination and quality of the products or a combination thereof.

Seed coating methods and compositions that are known in the art can be particularly useful when they are modified by the addition of one of the embodiments of the present invention. Such coating methods and apparatus for their application are disclosed in, for example, U.S. Pat. Nos. 5,918,413; 5,554,445; 5,389,399; 4,759,945; and 4,465,017. Various seed coating compositions are disclosed, for example, in U.S. Pat. Appl. Nos. US20110033432, US20100154299, U.S. Pat. Nos. 5,939,356; 5,876,739, 5,849,320; 5,791,084, 5,661,103; 5,580,544, 5,328,942; 4,735,015; 4,634,587; 4,372,080, 4,339,456; and 4,245,432, among others.

A variety of additives can be added to the seed treatment formulations comprising the inventive compositions. Binders can be added and include those composed preferably of an adhesive polymer that can be natural or synthetic without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

Any of a variety of colorants may be employed, including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. Other additives that can be added include trace nutrients such as salts of iron, manganese, boron, copper, cobalt, molybdenum and zinc. A polymer or other dust control agent can be applied to retain the treatment on the seed surface.

In some specific embodiments, in addition to the microbial cells or spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrins; alginates; sugars; molasses; polyvinyl pyrrolidones; polysaccharides; proteins; fats; oils; gum arabics; gelatins; syrups; and starches. More examples can be found in, for example, U.S. Pat. No. 7,213,367 and U.S. Pat. Appln. No. US20100189693.

Various additives, such as adherents, dispersants, surfactants, and nutrient and buffer ingredients, can also be included in the seed treatment formulation. Other conventional seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as calcium carbonate, gypsum, vermiculite, talc, humus, activated charcoal, and various phosphorous compounds.

In some embodiment, the seed coating composition can comprise at least one filler which is an organic or inorganic, natural or synthetic component with which the active components are combined to facilitate its application onto the seed. Preferably, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminum or magnesium silicates.

The seed treatment formulation may further include one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed or alternatively may be added as part of the seed coating composition of the invention.

Preferably, the amount of the novel composition or other ingredients used in the seed treatment should not inhibit germination of the seed, or cause phytotoxic damage to the seed.

The microorganism-treated seeds may also be further enveloped with a film overcoating to protect the coating. Such overcoatings are known in the art and may be applied using fluidized bed and drum film coating techniques.

In principle, any plant seed capable of germinating to form a plant that is susceptible to attack by nematodes and/or pathogenic fungi can be treated in accordance with the invention. Suitable seeds include those of cereals, coffee, cole crops, fiber crops, flowers, fruits, legume, oil crops, trees, tuber crops, vegetables, as well as other plants of the monocotyledonous, and dicotyledonous species. Preferably, crop seeds are coated which include but are not limited to bean, carrot, corn, cotton, grasses, lettuce, peanut, pepper, potato, rapeseed, rice, rye, sorghum, soybean, sugar beet, sunflower, tobacco, and tomato seeds. Most preferably, barley or wheat (spring wheat or winter wheat) seeds are coated with the present compositions.

Also provided, in another aspect of the present invention, is a novel cereal plant created by artificially introducing a microbial endophyte of the invention into a cereal plant that is free of endophytic microorganisms. In some embodiments of this aspect, the microbial endophyte introduced into the cereal plant may be an endophytic antagonist having suppressive activity against head blight disease or a causative agent of head blight disease. Furthermore, the endophytic antagonist introduced into the cereal plant may be the fungal strain SGI-010-H11. A variety of methods previously found effective for the introduction of a microbial endophyte into cereal grass species are known in the art. Examples of such methods include those described in U.S. Pat. Appl. No. 20030195117A1, U.S. Pat. Appl. No. 20010032343A1, and U.S. Pat. No. 7,084,331, among others. It will become apparent to those skilled in the art that many of the aforementioned methods can be useful for the making of a novel cereal plant of the invention.

After artificial infection, it is preferred that DNA of the isolated endophytic antagonist is amplified by PCR and the antagonist is confirmed by carrying out a homology search for the DNA amplified. Further it is preferred that a foreign gene that expresses an identifiable means is introduced into the above-mentioned endophytic antagonist, and the presence of the colonization of the above-mentioned endophytic antagonist infecting the plant is confirmed by the above-identifiable means using the foreign gene.

Preparing the Biocontrol Compositions According to the Present Invention

Cultures of the microbial antagonists may be prepared for use in the biocontrol compositions of the invention using standard static drying and liquid fermentation techniques known in the art. Growth is commonly effected in a bioreactor.

A bioreactor refers to any device or system that supports a biologically active environment. As described herein a bioreactor is a vessel in which microorganisms including the microbial antagonists of the invention can be grown. A bioreactor may be any appropriate shape or size for growing the microorganisms. A bioreactor may range in size and scale from 10 mL to liter's to cubic meters and may be made of stainless steel or any other appropriate material as known and used in the art. The bioreactor may be a batch type bioreactor, a fed batch type or a continuous-type bioreactor (e.g., a continuous stirred reactor). For example, a bioreactor may be a chemostat as known and used in the art of microbiology for growing and harvesting bacteria. A bioreactor may be obtained from any commercial supplier (See also Bioreactor System Design, Asenjo & Merchuk, CRC Press, 1995).

For small scale operations, a batch bioreactor may be used, for example, to test and develop new processes, and for processes that cannot be converted to continuous operations.

Microorganisms grown in a bioreactor may be suspended or immobilized. Growth in the bioreactor is generally under aerobic conditions at suitable temperatures and pH for growth. For the organisms of the invention, cell growth can be achieved at temperatures between 5 and 37° C., with the preferred temperature being in the range of 15 to 30° C., 15 to 28° C., 20 to 30° C., or 15 to 25° C. The pH of the nutrient medium can vary between 4.0 and 9.0, but the preferred operating range is usually slightly acidic to neutral at pH 4.0 to 7.0, or 4.5 to 6.5, or pH 5.0 to 6.0. Typically, maximal cell yield is obtained in 20-72 hours after inoculation.

Optimal conditions for the cultivation of antagonists of this invention will, of course, depend upon the particular strain. However, by virtue of the conditions applied in the selection process and general requirements of most microorganisms, a person of ordinary skill in the art would be able to determine essential nutrients and conditions. The microbial antagonists would typically be grown in aerobic liquid cultures on media which contain sources of carbon, nitrogen, and inorganic salts that can be assimilated by the microorganism and supportive of efficient cell growth. Preferred carbon sources are hexoses such as glucose, but other sources that are readily assimilated such as amino acids, may be substituted. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. Without being limited thereto, use of potato dextrose liquid medium for fungal antagonists and R2A broth premix for bacterial strains is preferred.

Throughout this disclosure, various information sources are referred to and incorporated by reference. The information sources include, for example, scientific journal articles, patent documents, textbooks, and World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

The discussion of the general methods given herein is intended for illustrative purposes only. Other alternative methods and embodiments will be apparent to those of skill in the art upon review of this disclosure, and are to be included within the spirit and purview of this application.

It should also be understood that the following examples are offered to illustrate, but not limit, the invention.

EXAMPLES

Example 1: Discovery of the Antagonistic Microorganisms Capable of Suppressing the Development of *Fusarium graminaerum* and *Gibberella zeae*, Causative Agents of Head Blight Disease This example describes a high-throughput process of collecting and screening candidate microorganisms that has been developed internally at Synthetic Genomics, Inc. to isolate strains of microorganisms having suppressive activity against causative agents of head blight disease, particularly against *Fusarium graminearum*. Novel microbial antagonistic strains were isolated from plant tissue samples collected from several locations across the United States. The bacterial strains SGI-014-C06, SGI-014-G01, SGI-015-F03, and SGI-015-H06 were isolated from plant root tissues collected from Eagle Peak Preserve near Julian, Calif. The fungal strain SGI-010-H11 and the bacterial strain SGI-005-G08 were isolated from stem tissues of two different plant samples collected from San Elijo Lagoon, Encinitas, Calif.

The microorganisms were isolated as follows. For bacterial strain isolation, plant root tissues were sonicated and subjected to serial dilutions on 2×YT (yeast extract and tryptone) and N-free agar medium plates. Individual colonies were then selected based on morphological characteristics, and individually cultured in liquid broth medium. For fungal isolation, plant tissue was first surface-sterilized by dipping in 70% ethanol and briefly passing through a flame. The tissue was then dissected and placed on potato dextrose agar (PDA) medium, followed by incubation at room temperature. When mycelial growth was observed, a segment of mycelial growth was then transferred to another PDA plate. Strains of microorganisms were isolated, purified and preserved at −80° C. in 15% glycerol at for bacterial strains and on dried barley seed for fungal strains.

Strains of microorganisms isolated as described above were thereafter assayed for their ability to suppress mycelial growth of *F. graminearum* in an in vitro antagonism test, which was performed on agar plates containing potato dextrose agar (PDA) growth medium according to a high-throughput screening procedure described in U.S. Pat. Appl. No. US20120107915A1, which is incorporated by reference herein, with minor modifications. Briefly, isolated strains of microorganisms were grown on one-fifth strength Tryptic soy broth agar (TSBA/5) for 24 hours prior to use. Conidial inoculum of *F. graminearum* NRRL-5883 was produced by hyphal tipping an actively growing colony of the fungus and transferring the hyphal strands to PDA agar medium. After incubating the plates for 7 days at 25° C. using a 12 h/day photoperiod, conidia were washed from PDA plates using a weak phosphate buffer (0.004% phosphate buffer, pH 7.2, with 0.019% $MgCl_2$). A suspension of conidia of *F. graminearum* in the weak phosphate buffer ($1 \times 10^5$ conidia/ml) was then immediately spread over the agar surface, and the plates were then incubated at 25° C. for 48-72 hours. To initiate the antagonism test, cells of isolated microbial strains were point-inoculated at equal distances inside the perimeter of the plate. After five days, the strains were scored as antibiosis positive when a visibly clear area that lacked mycelial growth existed around the perimeter of the microbial colonies.

More than 4,000 microbial strains were isolated and assayed by the procedure described above. Of those, six strains were found to significantly suppress the mycelial growth of *F. graminearum* NRRL-5883 on PDA medium. These new microbial antagonists are identified as SGI-005-G08, SGI-010-H11, SGI-014-C06, SGI-014-G01, SGI-015-F03, and SGI-015-H06.

Antagonism test was also performed for the new microbial antagonists for their ability to suppress the growth of fungal pathogen *Gibberella zeae*, which is a teleomorphic species of *Fusarium graminearum*. All procedures were identical to those described above, except that the pathogen strain tested in this assay was a pathogenic strain of the fungus *Gibberella zeae*. Of these six microbial antagonists, four strains SGI-010-H11, SGI-014-C06, SGI-015-F03, and SGI-015-1106 were found to significantly suppress the mycelial growth of *Gibberella zeae*.

Example 2: DNA Extraction, Sequencing and Taxonom

Fungal Cell Lysis and Acquiring ITS-5.8S rDNA Sequence Information

The fungal biomass was transferred to a 96-well PCR microplate containing 50 µl of a 2× lysis buffer (100 mM Tris HCL, pH 8.0, 2 mM EDTA, pH 8.0, 1% SDS, 400 µg/ml Proteinase K). Lysis conditions were as follows: 55° C. for 60 minutes, 94° C. for 4 minutes. An aliquot of the lysis product was used as the source of template DNA for PCR amplification. The ITS-5.8S rDNA sequence was amplified via PCR using two primers M13-ITS1 (SEQ ID NO: 15) and ITS4 M13-tailed (SEQ ID NO: 16).

For amplification of the ITS-5.8S rDNA region, each PCR mixture was prepared in a 20-µl final volume reaction containing 4 µl from the fungal lysis reaction, 0.2 µM of each primer (ITS1/ITS4), 6% Tween-20, and 10 µl of 2× ImmoMix (Bioline USA Inc, Taunton, Mass.). PCR conditions were as follows: 94° C. for 10 minutes; 94° C. for 30 seconds, 52° C. for 30 seconds, 72° C. for 75 seconds for 30 cycles; 72° C. for 10 minutes. A 2-µl aliquot of the PCR product was run on a 1.0% agarose gel to confirm a single band of the expected size. Positive bands were sent out for Sanger sequencing in the forward and reverse directions using M13 primers. Sequence of the 5.8S intergenic region (ITS) of the fungal strain SGI-010-H11 is provided in the Sequence Listing as SEQ ID NO: 11. Homology search for the determined nucleotide sequence of the 5.8S intergenic region (ITS) was conducted using the DDBJ/GenBank/EMBL database. Subsequently, the phylogenetic relationship of the nucleotide sequence of the 5.8S intergenic region (ITS) was analyzed among the isolated fungal antagonist SGI-010-H11 described herein, microorganisms of the genera and species that exhibit high sequence homologies to the isolated fungal antagonist SGI-010-H11, and other wide varieties of microorganism genera and species, using the ClustalW phylogenetic tree building program. The fungal strain SGI-010-H11 is considered to be related to the family of Mycosphaerellaceae based upon ~97% similarity of its ITS-5.8S rDNA sequence to those of *Mycosphaerella punctiformis* (GenBank EU343182) and *Ramularia pratensis* (GenBank EU019284), whose 5.8S ITS sequences show clear relatedness to Mycosphaerellaceae.

Bacterial Cell Lysis and Acquiring 16S rRNA Sequence Information

A 20 µl aliquot of cell suspension was transferred to a 96-well PCR plate containing 20 µl of a 2× lysis buffer (100 mM Tris HCL, pH 8.0, 2 mM EDTA, pH 8.0, 1% SDS, 400 µg/ml Proteinase K). Lysis conditions were as follows: 55° C. for 30 minutes, 94° C. for 4 minutes. An aliquot of the lysis product was used as the source of template DNA for PCR amplification. The 16S rRNA sequence was amplified via PCR using M13-27F (SEQ ID NO: 17) and 1492R M13-tailed (SEQ ID NO: 18) primers.

For amplification of 16S rRNA region, each PCR mixture was prepared in a 20-µl final volume reaction containing 4 µl from the bacterial lysis reaction, 2 µM of each primer (27F/1492R), 6% Tween-20, and 10 µl of 2× ImmoMix (Bioline USA Inc, Taunton, Mass.). PCR conditions were as follows: 94° C. for 10 minutes; 94° C. for 30 seconds, 52° C. for 30 seconds, 72° C. for 75 seconds for 30 cycles; 72° C. for 10 minutes. A 2-µl aliquot of the PCR product was run on a 1.0% agarose gel to confirm a single band of the expected size. Positive bands were sent out for Sanger sequencing in the forward and reverse directions using M13 primers. Sequences of the 16S rRNA of the bacterial strains SGI-014-C06, SGI-005-G08, SGI-014-G01, SGI-015-F03, and SGI-015-H06 are approximately 1.4-Kb in length and are provided in the Sequence Listing as SEQ ID NOs: 1, 10, 12, 13, and 14 respectively. Homology search for the determined nucleotide sequence was conducted using the DDBJ/GenBank/EMBL database. Subsequently, the phylogenetic relationship of the nucleotide sequence of the 16 rRNA genes was analyzed among the isolated bacterial antagonists described herein, bacteria of the genera and species that exhibit high sequence homologies to the isolated bacterial antagonists, and other wide varieties of bacterial genera and species, using the ClustalW phylogenetic tree building program. Sequence identity and similarity were also determined using GenomeQuest™ software (Gene-IT, Worcester Mass. USA). The sequence analysis result revealed that the bacterial isolate SGI-014-G01 can be considered to be related to the genus of *Variovorax* based upon ~99% similarity of its 16S rRNA sequence to those of several *Variovorax* species, including *Variovorax* sp. R-21938 (GenBank AJ786799) and *Variovorax paradoxus* (GenBank GU186109), whose 16S rRNA sequences show clear relatedness to *Variovorax* sp. Further, the sequence analysis result also revealed that the two bacterial isolates SGI-015-F03 and SGI-015-H06 can be considered to be related to the family of Bacillaceae, based upon >99% similarity of their respective 16S sequences to those of several *Bacillus* spp.

The sequence analysis result revealed that the two bacterial isolates SGI-014-C06 and SGI-055-G08 can be considered to be related to the family of Microbacteriaceae based upon >99% similarity of their respective 16S sequences to those of several *Microbacterium* spp. Notably, the 1430-nt sequence of the 16S rRNA gene of SGI-014-C06 (SEQ ID NO: 1) is identical to the 16S rRNA gene of a *Microbacterium oxydans* strain DSM 20578 and several other *Microbacterium* sp. strains (e.g., GenBank sequences Y17227.1, FJ200406, EU086800, and EU714335) over its entire 1430-nt length.

In particular, among the thousands of microbial strains that were isolated and tested for the ability to suppress *Fusarium* development in antagonism assays as described in Example 1, a total of eighty-eight strains was subsequently identified as *Microbacterium* species based upon the sequence similarity of their 16S sequences to those of known *Microbacterium* spp. However, Applicants have found that SGI-014-C06 and SGI-055-G08 were the only two *Microbacterium* strains that possessed suppressive activity against *Fusarium graminearum*. To date, as discussed above, several naturally occurring microbes have been reported as having antagonistic activity against head blight disease. However, there are no reports prior to the present invention that describe a microorganism of the genus *Mycobacterium* having such antagonistic activity. Further, prior to the present invention, the present inventors were not aware of any methods or processes of using a bacterial strain of the genus *Mycobacterium* as biocontrol agent in preventing, inhibiting or treating the development of a causative pathogen of head blight disease.

Example 3: Sequence Analysis of Housekeeping Genes from the Isolate SGI-014-C06

A phylogenetic study of several housekeeping genes from 27 species of the genus *Microbacterium* has been reported recently by Richert et al. (Syst. Appl. Microbiol. 30:102-108, 2007). The study concluded that although the merits of the 16S rRNA sequence analysis for systematic taxonomy are unsurpassed, sole emphasis on a single taxonomic parameter should not guide systematic conclusions. As disclosed above, the nucleotide sequence of the 16S rRNA gene of SGI-014-C06 (SEQ ID NO: 1) is identical to the 16S rRNA gene of several *Microbacterium* sp. strains, including the nucleotide sequence of a 16S rRNA gene of a *Microbacterium oxydans* strain DSM 20578 that was included in Richert et al. (2007) study (GenBank Accession Y17227.1). Applicants proceeded to perform a phylogenetic analysis on four housekeeping genes of the isolate SGI-014-C06, which are DNA gyrase subunit B (gyrB), RNA-polymerase subunit B (rpoB), recombinase A (recA), and polyphosphate kinase (ppk). Toward this end, the entire genome of the isolate SGI-014-C06 was shot-gun sequenced, assembled and annotated by using procedures described in PCT Patent Application No. WO2010115156A2. Genomic DNA was prepared from a fresh culture of SGI-014-C06. Cell pellet was used for high molecular weight DNA extraction using the UltraClean® Mega Soil DNA Isolation Kit (Cat. No 12900-10) from MO BIO Laboratories, Inc. according to the manufacture's recommended protocol. The genomic DNA from SGI-014-C06 was then prepared for shotgun 454-pyrosequencing. Genomic DNA (7.5 µg) was used for library construction according to the recommended protocol (454 Life Sciences) for single long reads. The sequences were generated by two GS FLX Titanium series sequencing runs.

The sequences of four housekeeping genes gyrB, rpoB, recA, and ppk of the isolate SGI-014-C06 are provided in the Sequence Listing. Homology search for the determined nucleotide sequences was conducted using the DDBJ/GenBank/EMBL database. Sequence identity and similarity were also determined using GenomeQuest™ software (Gene-IT, Worcester Mass. USA). As discussed in details below, the result of sequence analysis of the housekeeping genes revealed that the isolate SGI-014-C06 described in the present disclosure is a novel bacterial strain and can be considered to be related to the family of Microbacteriaceae.

The polynucleotide sequence of the gyrB gene of SGI-014-C06 has the greatest sequence identity with a gyrB gene of *Microbacterium testaceum* having GenBank accession number AP012052 (82.69% over a 936/2172 nucleotide alignment). When compared to the gyrB gene of the *Microbacterium oxydans* strain DSM 20578 (GenBank AM181493; Richert et al., 2007), the sequence homologies between the two genes were ~62% identical at the nucleotide level and ~37% identical at the amino acid level.

The polynucleotide sequence of the rpoB gene of SGI-014-C06 has the greatest sequence identity with an rpoB gene of *Microbacterium maritypicum* having GeneBank accession number AM181582 (96.98% over a 1093/3504 nucleotide alignment). When compared to the rpoB gene of the *Microbacterium oxydans* strain DSM 20578 (GenBank AM181583; Richert et al., 2007), the sequence homologies between the two genes were ~96% identical at the nucleotide level and 99% identical at the amino acid level.

The polynucleotide sequence of the recA gene of SGI-014-C06 has the greatest sequence identity with a recA gene of *Microbacterium testaceum* having GeneBank accession number AP012052 (85.45% over a 962/1188 nucleotide alignment). When compared to the recA gene of the *Microbacterium oxydans* strain DSM 20578 (GenBank AM181527; Richert et al., 2007), the sequence homologies between the two genes were ~92% identical at the nucleotide level and 100% identical at the amino acid level.

The polynucleotide sequence of the ppk gene of SGI-014-C06 has the greatest sequence identity with a ppk gene of *Microbacterium luteolum* having GenBank accession number AM181554 (91.38% over a 1380/2175 nucleotide alignment). When compared to the ppk gene of the *Microbacterium oxydans* strain DSM 20578 (GenBank AM181556; Richert et al., 2007), the sequence homologies between the two genes were ~91% identical at the nucleotide level and ~98% identical at the amino acid level.

Example 4: Protection of Wheat from *Fusarium graminearum* Infection Using the Microbial Antagonists *Microbacterium* sp. (NRRL B-50470) *Mycophaerella* Sp. (NRRL 50471), and *Variovorax* sp. (NRRL B-50469)

Microbial strains that were found positive for antibiosis in the antagonism screen described in Example 1 were further evaluated through a plant-based bioassay in which cells of the microbial strains were applied directly onto seeds of a susceptible cereal cultivar, followed by inoculation with conidial spores of *F. graminearum*. The microbial strains were grown to a sufficient turbidity and diluted in water. Two gram of wheat seeds of a susceptible wheat cultivar (Hank; WestBred LLC, Bozeman, Mont.) were sown in one-liter pots containing pasteurized soil medium. After sowing, 20 mL of the microbial culture dilution was transferred on top of sown seeds. The wheat seeds were allowed to germinate in greenhouse conditions under fluorescent lighting with a 14 hour photoperiod. At the onset of wheat flowering, the wheat heads were challenged by spraying with *F. graminearum* NRRL 5883 conidial spores. Conidial spores were harvested from five day old PDA plates by pouring water with 0.01% Tween20 on plates and scraping spores into suspension. After spraying spores, wheat plants were transferred to a mist chamber with 100% humidity for three days to allow for infection. The treatments were:

1. Untreated: no microbial or chemical fungicide treatment+*Fusarium* challenge.
 2. Non-infected: no microbial or chemical fungicide treatment, no *Fusarium* challenge.
 3. SGI-010-H11: fungal treatment+*Fusarium* challenge.
 4. SGI-014-G01: bacterial treatment+*Fusarium* challenge.
 5. SGI-014-C06: bacterial treatment+*Fusarium* challenge.

Twenty days after infection, watering was stopped and wheat plants were allowed to dry for three weeks before harvesting. Individual wheat heads were harvested and collected. Disease severity was determined for each head showing head blight disease symptoms. Disease severity was calculated as the number of diseased spikelets divided by the total number of spikelets per heads. The results (TABLE 2) revealed that wheat plants treated with each of the three microbial antagonists tested, SGI-014-C06 (NRRL B-50470), SGI-010-H11 (NRRL 50471), and SGI-014-G01 (NRRL B-50469), had significantly lower severity and incidence of *Fusarium graminearum* infestation when compared to the "untreated" control growing in the same conditions (P<0.05).

The seeds from each head were harvested by hand and the seed mass was weighed. The average seed weight per pot in each of the treatments was calculated. As reported in TABLE 3, each of the microbial antagonists was found to significantly reduce yield loss caused by head blight infestation.

TABLE 2

Efficacy of the microbial antagonists in reducing head blight incidence in wheat.

| Treatment | Percent severity (%) | STDEV | P value |
|---|---|---|---|
| Non-infected | 1.30 | 0.0025 | <.0001 |
| Untreated | 15.46 | 0.0364 | NA |
| SGI-010-H11 | 7.42 | 0.0219 | 0.0005 |
| SGI-014-G01 | 6.59 | 0.0315 | 0.0001 |
| SGI-014-C06 | 7.21 | 0.0225 | 0.0004 |

TABLE 3

Efficacy of the microbial antagonists in preserving seed yield in wheat plants having head blight disease.

| Treatment | Seed mass (g) | P value |
|---|---|---|
| Non-infected | 0.8438 ± 0.1633 | 0.0191 |
| Untreated | 0.4669 ± 0.1209 | NA |
| SGI-010-H11 | 0.6200 ± 0.1844 | 0.7025 |
| SGI-014-G01 | 0.7963 ± 0.2032 | 0.5277 |
| SGI-014-C06 | 0.6744 ± 0.0948 | 0.0551 |

Example 5: Growth Inhibition of *Fusarium graminearum* by Microbial Antagonists on Wheat Seedlings The microbial strains found to possess suppressive activity against *F. graminearum* in antagonism plate assay were investigated further for their ability to reduce the incidence of head blight in wheat. Seeds of a susceptible wheat cultivar (Hank; WestBred LLC, Bozeman, Mont.) were sown in 1-Liter pots each containing pasteurized soil medium in 20 cm diameter plastic pots. Microbial cell suspensions were prepared as follows. 2YT, or similar growth medium, broth cultures were inoculated from isolate glycerol stocks or streak plates. Typically, cultures were initiated 48-72 hours prior to use in the growth chamber, greenhouse or field allowing the culture to reach late exponential phase. Isolates that have longer doubling times were initiated further in advance. Cultures were incubated at 30° C. on a rotary shaker at 200 rpm. After growth, the cells were pelleted at 10,000×g for 15 min at 4° C. and re-suspended in 10 mM $MgSO_4$ buffer (pH 7.0). Cell densities were normalized for each isolate on a CFU/mL basis (cell performing units per milliliter). Typically, ~$10^9$ CFU/mL suspensions were prepared for each isolate and transported to the inoculation site on ice. Inoculations were performed by diluting these cell suspensions $\frac{1}{20}$ in irrigation water to a final density $5×10^7$ CFU/mL. For 1-L pot trials, 20 mL of this dilute cell suspension was distributed evenly over the surface of each replicate pot. For micro-trial pots, cell suspensions were not diluted and 1 mL of each $10^9$ CFU/mL suspension was pipetted directly onto the surface of each replicate pot as soil drench on top of the submerged seeds. The seeds and plants were maintained in a greenhouse at room temperature with a 14 h photoperiod of light.

Mycelium of the *Fusarium graminearum* strain NRRL-5883 was grown on PDA plates for 5 days under constant light. Hyphae and conidia were harvested by pouring a few mL of sterile water (0.01% Tween 20) on the plates and scraping the agar surface with a sterile spatula. The concentration of spores in the inoculum was approximately $2×10^5$ spores/mL, but hyphal fragment concentration was not determined.

Inoculation with *F. graminearum* began after shoot emerging from the seeds and continued every other evening for 10 days. The inoculum of *F. graminearum* was applied with a sprayer at about 30 mL per pot. Immediately after each inoculation, the plants were misted with overhead mister. When chemical fungicide was used, the fungicide (Banner Maxx, Syngenta) was prepared by diluting 2 mL of fungicide stock in 1 L of distilled water, and was applied with a sprayer at about 30 mL per pot.

Head blight was evaluated by the severity of *Fusarium* infestation, as determined by the number of *Fusarium* colony-forming units per gram (CFU/g) of plant tissues. All treatments were performed in four blocks with four replicate pots. The treatments were:

1. Untreated: no microbial or chemical fungicide treatment, +*Fusarium* challenge
2. Non-infected: no microbial or chemical fungicide treatment, no *Fusarium* challenge.
3. Fungicide: chemical fungicide treatment+*Fusarium* challenge.
4. SGI-010-H11: fungal treatment+*Fusarium* challenge.
5. SGI-014-G01: bacterial treatment+*Fusarium* challenge.
6. SGI-014-C06: bacterial treatment+*Fusarium* challenge.

The results, as reported in TABLE 4, revealed that all three microbial treatments provided a significant decrease in FHB severity as compared to the infected control. In particular, two microbial antagonists, SGI-014-C06 and SGI-010-H11, significantly reduced the infestation of wheat plants by *Fusarium graminearum* when compared to the untreated control grown in the same conditions. The protection of wheat plants from *Fusarium* infestation effected by each of the two microorganisms SGI-014-C06 and SGI-010-H11 was statistically comparable to the protection effected by the commercial chemical fungicide. When the microorganism SGI-014-G01 was applied, the observed protection of wheat plants from *Fusarium* infestation was much less conspicuous and its effectiveness varied greatly among the replicate pots.

TABLE 4

Effect of microbial antagonists on *Fusarium* infestation.

| Treatment | CFU/g | P value |
|---|---|---|
| Untreated | 1487 ± 600 | N/A |
| Non-infected | 0 ± 0 | <.0001 |

TABLE 4-continued

Effect of microbial antagonists on *Fusarium* infestation.

| Treatment | CFU/g | P value |
|---|---|---|
| Chemical fungicide | 290 ± 146 | <.0001 |
| SGI-010-H11 | 671 ± 450 | 0.0077 |
| SGI-014-G01 | 1246 ± 465 | 0.8387 |
| SGI-014-C06 | 367 ± 234 | 0.0001 |

Example 6: Growth and Storage of the Microbial Antagonists

*Mycosphaerella* sp.: Several methods were used to store the isolated fungus as a pure culture, one of which was the filter paper technique. The fungus was also allowed to grow on PDA, and then it was cut into small squares which were placed into vials containing 15% glycerol and stored at −70° C. The fungus was also stored at 4° C. by a similar method, using distilled water rather than glycerol. However, one of the preferred methods of storage was on infested sterile barley seed at −80° C.

*Bacillus* sp., *Microbacterium* sp. and *Variovorax* sp.: The isolated bacteria were stored as a pure culture. A bacterial colony was transferred to a vial containing R2A broth liquid medium (Tecknova) and allowed to grow at 30° C. with shaking at 250 rpm for two days. The culture was then transferred into vials containing 15% glycerol and stored at −80° C.

Example 7: Spore Production and Seed Coating Treatments

Spore Production:

In a typical spore production procedure, one liter of 2×YT growth medium (16 g/L Tryptone, 10 g/L yeast extract, 5 g/L NaCl) was inoculated with 5 mL starter culture or petri dish scraping and incubated overnight at 30° C. in a rotating shaker that was set at 225 rpm. Bacterial cells were pelleted by centrifugation, and washed 1× with PBS buffer (8 g/L NaCl; 0.2 g/L KCl; 1.44 g/L $Na_2HPO_4$; 0.24 g of $KH_2PO_4$; pH 7.4). Cells were resuspended in CDSM medium (Hageman et al., *J. Bacteriol.*, 438-441, 1984), and were grown for four additional nights at 30° C. in the rotating shaker. Sporulation in the bacterial culture was monitored daily by using phase contrast microscope until the entire culture was virtually made up of free-floating spores. The incubation time typically took less than four days or more than six days depending on the species. Under phase contrast microscope, endospores were detected within cells as bright white oblate spheroids. Bacterial spores were pelleted by centrifugation at 10,000×g for 15 minutes, washed two times with sterile $dH_2O$ and, if necessary, concentrated down to 50 mL and could either be used immediately or refrigerated for later use. Spore concentration was measured at $OD_{600}$. This procedure typically produced at least 2000 OD's of bacterial spores.

In particular, several bacterial strains of the present invention, e.g. *Bacillus* sp. SGI-015-F03, could conveniently produce large amounts of spores after 4 days of incubation with a simple inoculation of a large overnight starter culture (~15 mL) in to 1 liter of 2×SG growth medium, followed by a 4-day incubation at appropriate temperature in a rotating shaker set at 225 rpm. The recipe of the 2×SG growth medium was as follows: 16 g/L Nutrient Broth; 0.25 g/L $MgSO_4$; 2.0 g/L KCl; 0.15 g/L $CaCl_2.2H_2O$; 0.025 g/L $MnCl_2.2H_2O$; 0.28 mg/L $FeSO_4.7H_2O$; 1.0 g/L Dextrose.

Seed Coating Treatments of Wheat and Corn Seeds:

Small-scale seed treatment experiments were conducted by following a procedure described in Sudisha et al., 2009 with minor modifications. Typically, a biopolymer stock solution was made by adding 6 gram of gum Arabic powder (MP Biomedical) to 36 mL water in a 50 mL Falcon tube, which was subsequently mixed to homogeneity by using a wheel mixer. A stir plate was used for mixing when larger quantities of coated seeds were needed.

When vegetative cells were used, turbid cultures of actively growing microbial cells were washed with PBS and adjusted to an $OD_{600}$ of ~5.0. Alternatively, microbial spore suspensions were prepared as described above. Bacterial spores and/or vegetative cells were thoroughly resuspended in ~32 mL gum Arabic biopolymer stock solution prepared as described above, and resulting suspension was mixed thoroughly in a 1 L bottle. Approximately 400 g of seeds (either wheat or corn) were added to the bottle and vigorously shaken or vortexed to ensure a uniform distribution of the gum/cell suspension. Coated seeds were then spread across a sterile plastic weigh boats to dry in a laminar flow hood until no longer tacky, generally 3-6 hours with periodic mixing. In some instances, seeds coated with spores could be dried overnight. However, seeds coated with vegetative cultures were typically stored away before they completely desiccated. Viability test performed periodically on the microbes used in seed coating formulation showed that the microbes remained viable for at least three months. Germination rate of the coated seeds was determined to be essentially identical to control uncoated seeds.

Example 8: Effect of Microbial Seed Treatments on the Development of *Fusarium* Head Blight in Wheat Seeds of a FHB-susceptible wheat cultivar (RB07) were coated with each of the microorganisms SGI-014-C06; SGI-015-F03, and SGI-015-H06, in accordance with the procedure described in Example 8. Coated seeds were subsequently sown in one-liter pots containing pasteurized soil medium [(Metromix-Mix 200; Scotts-Sierra Horticultural Products, Marysville, Ohio; and 3 gram of fertilizer 14-14-14 (N-P-K)]. Pots were seeded at 7-8 plants per pot and subsequently thinned to 5 plants per pot at the 3-leaf stage. Pots were arranged in randomized blocks with 5 pots per treatments. The coated seeds were then allowed to germinate in greenhouse conditions under fluorescent lighting with 16 hours of lighting per day. At the onset of wheat flowering (anthesis), the wheat heads were challenged by spraying with *F. graminearum* NRRL 5883 macroconidial spores at a concentration of 100,000 spores/mL. After spraying spores, wheat plants were transferred to a dew chamber with 100% humidity for three days to allow for infection. The treatments were:

1. Untreated: no microbial or chemical fungicide treatment+*Fusarium* challenge.

2. SGI-014-C06: bacterial seed treatment+*Fusarium* challenge.

3. SGI-015-F03: bacterial seed treatment+*Fusarium* challenge.

4. SGI-015-H06: bacterial seed treatment+*Fusarium* challenge.

Severity of head blight disease was assessed visually at ten days and twenty-one days after infection. Disease severity was determined for each spike showing head blight disease symptoms, and calculated as the percentage of symptomatic spikelets; i.e. the number of spikelets displaying FHB symptoms divided by the total number of spikelets. The results (TABLE 5) revealed that wheat seeds coated with each of the three microbial antagonists tested, SGI-014-C06; SGI-015-F03, and SGI-015-H06, had significantly lower severity of *Fusarium graminearum* infestation when compared to the "untreated" control growing in the same conditions (P<0.05).

TABLE 5

Development of head blight symptoms in wheat following seed treatments with antagonistic microorganisms

| Treatment | Infection severity (%) | |
|---|---|---|
| | 10 days post-infection | 21 days post infection |
| Untreated control | 49.31 | 66.10 |
| SGI-014-C06 | 2.08 | 7.74 |
| SGI-015-F03 | 23.12 | 31.53 |
| SGI-015-H06 | 9.42 | 19.81 |

Example 9: Biocontrol of Head-Blight Disease of Wheat in Greenhouse Trials

Each of the microorganisms SGI-014-C06; SGI-015-F03, and SGI-015-H06 were further tested at larger-scale greenhouse trials. The trials were conducted in a "plant growth containment room" (PGCR) located at Synthetic Genomics, Inc., and included the following control treatments: infected control, non-infected control, as well as four commercial fungicide benchmarks. The benchmarking chemical fungicides were Banner MAXX® (Syngenta) at a concentration of 2 ml/L and Prosaro® (Bayer CropScience) at a concentration of 3 ml/L, each applied as a foliar spray, following manufacturers' recommendation. The benchmarking biological fungicides were Actinovate® (Natural Industries) and RhizoVital® (ABiTEP GmbH), each applied as a soil drench as per instruction manuals recommended by manufacturers.

The microbial treatments were prepared and applied either as a soil drench or as a seed coat. When microbial treatments were applied as a soil drench, cell suspensions of each of the microorganisms were individually applied to the seeds before covering the seeds with more growth medium. For this purpose, freshly prepared cultures were pelleted to remove growth media and resuspended in 10 mM magnesium sulfate ($MgSO_4$) buffer. Cell suspensions were then added by pipetting and distributing 20 milliliters evenly across the seeds at a total cell number of ~$10^9$ cells per pot. When microbial treatments were applied as a seed coating, microorganism cells/spores were essentially prepared as described in Example 8 above. Coated seeds were produced by incorporating cell suspensions with a gum Arabic solution to form a tacky coating mixture that was subsequently applied to the seeds. The microbial seed coating was then allowed to dry to form a hard but water soluble biopolymer entrapping the microorganism cells/spores. The goal was to reach a cell titer in the range of at least $10^6$-$10^7$ viable cells/seed. In this greenhouse trial experiment, the seed coatings were prepared the day prior to the sowing of the seeds.

Each treatment had four replicates that were positioned in a Randomized Complete Block Design (RCBD) on three leveled racks arranged in two rows along the sides of a growth room. The racks were equipped with fluorescent lights (Agrosun, 5850K) that generated on average 800 mole of light intensity as measured at the pot surface. Each replicate consisted of four 1-liter pots contained in a half flat. The pots were filled with a synthetic growth medium consisted of a 3:1 ratio (v/v) of *Arabidopsis* Growth Medium AIS (Lehle Seeds) to sand (Washed Coarse). In each pot, two grams of spring wheat seeds (Hank, WestBred) were scattered on the surface of the growth medium. The pots were bottom watered by keeping ~2 cm water at their base and observed for germination and growth.

At flowering stage (Feekes 10.5.1) the wheat heads were infected by spraying with a *Fusarium graminearum* conidial spore suspension. For this greenhouse trial experiment, fungal spores were prepared by plating homogenized mycelia of *F. graminearum* strain NRRL 5883 onto large PDA plates, followed by five-day incubation under constant light at room temperature. The fungal spores were then harvested by flooding the plates with magnesium sulfate buffer (10 mM $MgSO_4$; 0.01% Tween 20) and gently scraping the agar surface with a sterile spatula. The spore concentration was adjusted and approximately 50,000 conidial spores were applied per head with a pressurized hand sprayer. The growth room relative humidity was increased to 90% for three days allowing for infection before again being normalized. After wheat seeds had set, watering was stopped and the wheat heads were allowed to dry completely. Individual wheat heads were harvested and collected. Disease severity was determined for each wheat head showing head blight disease symptoms. Disease severity was calculated as the number of diseased spikelets divided by the total number of spikelets per head. The results (TABLE 6) revealed that wheat treated with each of the three microbial antagonists tested, SGI-014-C06; SGI-015-F03, and SGI-015-1106, had significantly lower severity and incidence of *Fusarium graminearum* infestation when compared to the "untreated" control growing in the same conditions ($P<0.05$).

TABLE 6

Efficacy of the microbial antagonists in reducing head blight incidence in wheat.

| Treatment | Infection severity (%) | Infection protection % |
|---|---|---|
| Non-infected | 2.1 ± 2.9 | N/A |
| Infected | 37.2 ± 9.8 | 0.00 |
| Prosario ® | 4.6 ± 2.8 | 93.00 |
| Banner-MAXX ® | 12.5 ± 5.8 | 70.00 |
| Actinovate ® | 38.9 ± 12.1 | −5.00 |
| RhizoVital ® | 28.0 ± 5.4 | 26.00 |
| SGI-014-C06 | 18.4 ± 9.1 | 30.00 |
| SGI-015-F03 | 25.4 ± 6.9 | 54.00 |
| SGI-015-H06 | 26.6 ± 7.4 | 34.00 |

To determine seed yield, wheat heads were individually threshed by hand, the seeds collected and cleaned of chaff and other detritus, counted, and weighed. The total seed yield was determined as the total seed mass produced by 16 pots of each of the treatments. As reported in TABLE 7 each of the three microbial antagonists tested was found to significantly protect the seed yield; i.e. the yield loss caused by head blight infestation was significantly reduced.

TABLE 7

Efficacy of the microbial antagonists in preserving seed yield in wheat plants having head blight disease.

| Treatment | Total seed yield (g) | Yield protection (%) |
|---|---|---|
| Non-infected | 14.36 | N/A |
| Untreated | 11.05 | 0.00 |
| Prosario ® | 13.44 | 72.00 |
| Banner-MAXX ® | 14.41 | 102.00 |
| Actinovate ® | 11.99 | 28.00 |
| RhizoVital ® | 12.65 | 48.00 |
| SGI-014-C06 | 14.70 | 110.00 |
| SGI-015-F03 | 15.03 | 120.00 |
| SGI-015-H06 | 14.14 | 93.00 |

Thus, treatments of wheat plants with each of the tested microorganisms significantly preserved the wheat plants against yield loss caused by *Fusarium* infestation. In particular, wheat plants treated with either SGI-014-C06 or SGI-015-F03 showed a significant improvement in total seed yield; i.e. 110% and 120% respectively, when compared to non-infected control. In contrast, the benchmarking fungicides Actinovate®, RhizoVital®, and Prosario® did not appear to significantly protect the treated wheat plants from yield loss caused by *Fusarium* head blight infestation.

Example 10: Biocontrol of Wheat Scab Under Field Conditions

Microorganism antagonists that were found having suppressive activity against the pathogen *F. graminearum* and head blight disease in in vitro antagonism assays and greenhouse studies, as described in Examples 4-9, are further evaluated in a series field experiments at different geographical locations throughout the United States. Some experiments are carried out in agricultural areas which are used for microbiological control of wheat scab, where natural disease infection occurs. The wheat variety used in the test is a *F. graminearum* susceptible variety. Generally, wheat plants with each treatment were sown in plots of 12 rows, about 3-meters long. The space between rows is about 20 cm. Treated plots in each experiment are arranged in a randomized block design. The efficacy of various wettable powder compositions containing the microbial antagonists of the present invention in reducing head blight severity and incidence are also assessed. In these experiments, the microbial antagonists are evaluated either individually or in combination.

In these tests, microorganism antagonists are evaluated in various seed-coating treatments and/or field tests where microbial suspensions are applied directly onto flowering wheat heads. In each of the experiments, the microorganisms are assessed in replicated plots. Antagonist, pathogen, and plant production methods as described in Examples 4-9 can be used in these experiments.

Seed-coating treatment—In addition to the seed coating method described in Example 7 above, a variety of techniques and seed-coating formulations known in the art can be deployed for the treatment of wheat seeds with microbial antagonists, such as those described previously by Fernando et al., 2002; Bello et al., 2002; and Kim et al., 1997. In general, wheat seeds are pre-moistened and stored at room temperature to promote germination. Germinated seeds can be then immersed into microbial suspensions before seeding. The pathogen spores can be inoculated either before or after bacterial inoculation. Antagonist, pathogen, and plant production methods as described in Examples 4 and 5 can be used for these seed treatments.

Disease severity and yield assessment—The antagonists are subjected to further evaluation in greenhouse and field evaluation for their suppressive activity against head blight disease on wheat and barley at flowering stages, by using a variety of methods and procedures, typically those described in, e.g., Schisler, *Plant Disease*, Vol 86(12), 1350-1356, 2002; Schisler et al. *Biological Control,* 39:497-506, 2006; and Khan and Doohan, *Biological Control,* 48:42-47, 2009. In one of such experiments, inoculums of *G. zeae* are prepared on sterile, yellow dent corn as described by Khan et al. (*Biological Control,* 29:245-255, 2004). Fully colonized lipid cultures (48-hour culture) of microbial strains are diluted to one-quarter strength with phosphate buffer. Final CFU per mL counts for antagonist treatments are between $1\times10^9$ CFU/mL and $6\times10^9$ CFU/mL. Treatment suspensions are then applied to flowering wheat heads using a $CO_2$ backpack sprayer. Treatments are typically applied after sunset to minimize potential UV degradation of antagonist cells. There are 5 replicates per treatment which are arranged in a randomized block design. The primary control treatment consists of plants treated with a buffer solution. A second control consists of untreated plants. Field assessments of head blight disease and incidence are made by evaluating 60 heads per replicate (L e. 300 heads/treatment) when plant development reaches between mid-milk and soft dough development. Wheat heads are harvested by hand and threshed using an Almaco single plant and head thresher (Almaco, Iowa) when grains reach full maturity. Grain samples obtained from each replicate row are evaluated for 100-kernel weight. Disease severity, incidence, and 100-kernel weight data are analyzed using one-way analysis of variance (ANOVA).

The compositions containing the microbial antagonists of the invention, either individually or in combination, are found to significantly diminish the disease incidence. These results show that the biological control measures using these active microbial agents can play an important role in the management of scab on cereal plants such as wheat plants.

Example 11: Development of Non-Naturally Occurring Cultivars and Breeding Program Endophytic microorganisms of the present invention are introduced into crop plants, including cereals, of varying genotypes and geographic origin, lacking such endophytic microorganisms, to create plant-endophyte combinations with improved agronomic characteristics, using procedures analogous to those known in the art, including those described in U.S. Pat. Appl. No. 20030195117A1; U.S. Pat. Appl. No. 20010032343A1; and U.S. Pat. No. 7,084,331, among others. Thus, given synthetic plant-endophyte combinations may be created and selected in a breeding/cultivar development program based on their ability to form and maintain a mutualistic combination that results in an agronomic benefit. Rating of agronomic characteristics of the combination may also be utilized in such a breeding program. These characteristics may include, without limitation, drought tolerance, biomass accumulation, resistance to insect infestation, palatability to livestock (e.g. herbivores), ease of reproduction, and seed yield, among others. Such combinations may differ in levels of accumulation of microbial metabolites that are toxic to pests and weeds, including ergot alkaloid levels, loline levels, peramine levels, or lolitrem levels, while displaying desired agronomic characteristics of crop plants, including resistance to insect feeding or infestation, resistance to abiotic stress, palatability to livestock, biomass accumulation, ease of reproduction, and seed yield, among other traits.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Headings within the application are solely for the convenience of the reader, and do not limit in any way the scope of the invention or its embodiments.

All publications and patent applications mentioned in this specification are herein incorporated by reference to the same extent as if each individual publication or patent application was specifically can individually indicated to be incorporated by reference.

What is claimed is:

1. A freeze dried or lyophilized composition comprising *Mycosphaerella* sp. strain SGI-010-H11 (deposited as NRRL 50471) or a pesticidally active variant thereof comprising a 16S rRNA nucleic acid sequence comprising a polynucleotide sequence having at least 98% sequence identity to the polynucleotide sequence of SEQ ID NO:11 and an agriculturally effective amount of a pesticide selected from the group consisting of an acaricide, a bactericide, a fungicide, an insecticide, a microbicide, and a nematicide, wherein the composition exhibits pesticidal activity.

2. A composition comprising *Mycosphaerella* sp. strain SGI-010-H11 (deposited as NRRL 50471) or a pesticidally active variant thereof comprising a 16S rRNA nucleic acid sequence comprising a polynucleotide sequence having at least 99% sequence identity to the polynucleotide sequence of SEQ ID NO:11 and a carrier, wherein the carrier comprises an adherent that confers increased stability, wettability or dispersability relative to a composition lacking the carrier, wherein the composition exhibits pesticidal activity, wherein the adherent comprises a polyvinyl acetate, a polyvinyl acetate copolymer, a polyvinyl alcohol, a polyvinyl alcohol copolymer, a methyl cellulose, a hydroxymethyl cellulose, and/or a hydroxymethyl propyl cellulose.

3. The composition according to claim 2, wherein said carrier is an agriculturally acceptable carrier.

4. The composition according to claim 2, wherein said carrier comprises a plant seed.

5. The composition according to claim 2, wherein said composition is prepared as a formulation selected from the group consisting of a colloid, a dust, a granule, a pellet, a powder, a spray, an emulsion, and a solution.

6. The composition according to claim 2, wherein said composition is a seed coating formulation.

7. A seed having a coating comprising a seed coating formulation, the seed coating formulation comprising *Mycosphaerella* sp. strain SGI-010-H11 (deposited as NRRL 50471) or a pesticidally active variant thereof comprising a 16S rRNA nucleic acid sequence comprising a polynucleotide sequence having at least 99% sequence identity to the polynucleotide sequence of SEQ ID NO:11 and a carrier, wherein the carrier comprises an adherent that confers increased stability, wettability or dispersability relative to a composition lacking the carrier, wherein the composition exhibits pesticidal activity.

8. A method for preventing, inhibiting or treating the development of head blight disease of a plant, wherein said method comprises applying to the plant, or to the plant's surroundings, an effective amount of the composition of claim 2.

9. The method according to claim 8, wherein said composition is applied to soil, a seed, a root, a flower, a leaf, a portion of the plant, or the whole plant.

10. The method according to claim 8, wherein said plant is susceptible to *Fusarium graminearum*.

11. The method according to claim 8, wherein said plant is a wheat plant, a corn plant, a barley plant, or an oat plant.

12. The method according to claim 8, wherein said *Mycosphaerella* sp. strain is an endophyte on said plant.

13. A plant that is dusted, coated, injected, rubbed, rolled, dipped, sprayed, or brushed with the composition of claim 7.

14. A seed, a reproductive tissue, a vegetative tissue, plant parts, or progeny of the plant of claim 13, wherein the seed, reproductive tissue, vegetative tissue, plant parts, or progeny is dusted, coated, injected, rubbed, rolled, dipped, sprayed, or brushed with the composition.

15. The freeze dried or lyophilized composition of claim 1, wherein said polynucleotide sequence has at least 99% sequence identity to the polynucleotide sequence of SEQ ID NO:11.

16. The freeze dried or lyophilized composition of claim 1, wherein said polynucleotide sequence comprises the polynucleotide sequence SEQ ID NO:11.

17. The composition of claim 2, wherein said polynucleotide sequence comprises the polynucleotide sequence of SEQ ID NO:11.

18. The seed of claim 7, wherein said polynucleotide sequence comprises the polynucleotide sequence of SEQ ID NO:11.

* * * * *